(12) United States Patent
Paxson et al.

(10) Patent No.: US 8,296,070 B2
(45) Date of Patent: Oct. 23, 2012

(54) METHOD AND APPARATUS FOR IMPROVED SIMULATION OF CHEMICAL AND BIOCHEMICAL REACTIONS

(75) Inventors: Ricardo E. Paxson, Boston, MA (US); Joseph F. Hicklin, Upton, MA (US)

(73) Assignee: The MathWorks, Inc., Natick, MA (US)

( * ) Notice: Subject to any disclaimer, the term of this patent is extended or adjusted under 35 U.S.C. 154(b) by 1663 days.

(21) Appl. No.: 10/783,624

(22) Filed: Feb. 20, 2004

(65) Prior Publication Data
US 2005/0187747 A1    Aug. 25, 2005

(51) Int. Cl.
*G01N 33/50*    (2006.01)
*G01N 33/48*    (2006.01)

(52) U.S. Cl. ............................................ 702/19; 702/20
(58) Field of Classification Search .................. None
See application file for complete search history.

(56) References Cited

U.S. PATENT DOCUMENTS

| | | | |
|---|---|---|---|
| 5,930,154 | A | 7/1999 | Thalhammer-Reyero |
| 5,980,096 | A | 11/1999 | Thalhammer-reyero |
| 6,219,440 | B1 | 4/2001 | Schaff et al. |
| 2002/0022947 | A1* | 2/2002 | Kurata ............................. 703/2 |
| 2003/0215786 | A1 | 11/2003 | Hill et al. |

OTHER PUBLICATIONS

Sauro et al. (Omics: A Journal of Integrative Biology, vol. 7, No. 4, Dec. 2003).*
Hucka et al. (Pacific Symposium on Biocomputing vol. 7, p. 450-461, 2002).*
Loew, Leslie M., "The Virtual Cell project," *Novartis Foundation Symposium*, vol. 247:151-161 (2002).
Vayttaden, Sharat Jacob et al, "Developing Complex Signaling Models Using GENESIS/Kinetikit," *Science's stke*, retrieved online at http://www.stke.org/cgi/content/full/sigtrans;2004/219/p14.
International Search Report for Application No. PCT/US2005/005303, dated Mar. 20, 2006.
Goryanin, Igor et al., "Mathematical simulation and analysis of cellular metabolism and regulation," *Bioinformatics*, vol. 15(9):749-758 (1999).
Slepchenko, Boris M. et al., "Computational Cell Biology: Spatiotemporal Simulation of Cellular Events," *Annu. Rev. Biophys. Biomol. Struct.*, vol. 31:423-441 (2002).
You, Lingchong et al., "Modeling biological systems using Dynetica—a simulator of dynamic networks," *Bioinformatics*, vol. 19(3):435-436 (2003).

* cited by examiner

*Primary Examiner* — Jason Sims
(74) *Attorney, Agent, or Firm* — Nelson Mullins Riley & Scarborough LLP

(57) ABSTRACT

An integrated system for modeling, simulating and analyzing chemical and biochemical reactions includes a modeling environment for constructing a model of a chemical or biochemical reaction. The system also includes a simulation engine accepting as input said constructed model of the chemical or biochemical reaction and generating as output an expected result for a first chemical reaction using a first type of computational model and an expected result for a second chemical reaction using a second type of computational model. An analysis environment communicates with the simulation engine and displays the expected result.

20 Claims, 10 Drawing Sheets

Fig. 3B

METHOD AND APPARATUS FOR IMPROVED SIMULATION OF CHEMICAL AND BIOCHEMICAL REACTIONS

FIELD OF THE INVENTION

The present invention relates to simulation tools and, in particular, to an improved system for simulating chemical and biochemical reactions.

BACKGROUND OF THE INVENTION

Development of new chemical and biochemical substances is time-consuming because a number of intermediate substances are traditionally formulated before formulation of a substance with the desired properties is obtained, and formulation of each intermediate substance can takes hours or days. Chemical formulation includes manufacture of traditional organic or polymer substances, as well as the development of small-molecule machinery, sometimes referred to as nano-machinery. Biochemical formulation includes the development and analysis of pharmaceutical substances that affect an individual's quality of life. In addition to the tedious and often error-prone nature of chemical and biochemical formulation, both of these fields face additional difficulties.

Development of chemical substances and nanomachinery, in addition to being time-consuming, can generate potentially dangerous intermediate substances. For example, in attempting to formulate bacteria that consumes crude oil and breaks it down into one or more environmentally-friendly substances, a researcher may formulate a bacterium that breaks crude oil into a number of environmentally-friendly substances and a lethal toxin. Additionally, chemical researchers are faced with the problem of disposing of the intermediate products generated by their research. Other issued faced by designers of nanomachinery is that the target substance may mutate during formulation in response to environmental factors.

Biochemical research, which typically focuses on identifying and selecting compounds having the potential to affect one or more mechanisms thought to be critical in altering specific clinical aspects of a disease processes faces challenges in addition to the ones described above.

Although drug development is typically motivated by research data regarding cellular and subcellular phenomena, the data often considers only an isolated and rather narrow view of an entire system. Such data may not provide an integrated view of the complete biological system. Moreover, the narrow findings reported are not always entirely accurate when translated to the whole body level.

Moreover, current methods of obtaining data for biological processes are even more time-consuming than those associated with chemical processes, because the latter for biochemical substances generally require laboratory experiments that lead to animal experiments and clinical trials. From these trials and experiments, data are obtained which, again, usually focus on a very narrow part of the biological system. Only after numerous costly trial-and-error clinical trials, and constant redesigning of the clinical use of the drug to account for lessons learned from the most recent clinical trial, is a drug having adequate safety and efficacy finally realized. This process of clinical trial design and redesign, multiple clinical trials and, in some situations, multiple drug redesigns requires great expense of time and money. Even then, the effort may not produce a marketable drug. While conclusions may be drawn by assimilating experimental data and published information, it is difficult, if not impossible, to synthesize the relationships among all the available data and knowledge.

The various challenges faced by chemical and biochemical researchers make it desirable to have systems and methods for modeling, simulating, and analyzing biological processes in-silico rather than in-vivo or in-vitro.

BRIEF SUMMARY OF THE INVENTION

In one aspect the present invention relates to a system that integrates modeling, simulation and analysis of a biological system or chemical reactions. The system includes a modeling component for constructing a model of a biological system or a chemical reaction. The systems also includes a simulation engine accepting as input said constructed model of the chemical or biochemical reaction and generating as output an expected result. An analysis environment communicates with the simulation engine and displays the expected result. In some embodiments, the modeling component allows construction of a block diagram model of a biological system or a chemical reaction. In some of these embodiments, the modeling component includes at least one block identifying a set of related chemical reactions.

In another aspect the present invention relates to a method for integrated modeling, simulation and analysis of a biological system or chemical reactions. A graphical user interface for accepting user commands and data is provided and user commands and data are received via the provided user interface. The received user commands and data are used to construct a model of the biological system or the chemical reaction, which is used to generate dynamic behavior of the modeled biological system or chemical reactions. The expected result is then displayed.

In still another aspect the present invention relates to an article of manufacture having embodied thereon computer-readable program means for integrated modeling, simulation and analysis of a biological system or a chemical reaction. Embodied on the article of manufacture are computer-readable program means for providing a graphical user interface for accepting user commands and data; computer-readable program means for receiving, via the provided user interface, user commands and data; computer-readable program means for constructing, using the received user commands and data, a model of the biological system or the chemical reaction; computer-readable program means for generating, using the constructed model of the chemical or biochemical reaction, dynamic behavior of the modeled biological system or chemical reaction; and computer-readable program means for displaying the expected result.

BRIEF DESCRIPTION OF THE DRAWINGS

The invention is pointed out with particularity in the appended claims. The advantages of the invention described above, and further advantages of the invention, may be better understood by reference to the following description taken in conjunction with the accompanying drawings, in which:

FIGS. 3A and 3B are screenshots depicting embodiments of a tabular modeling environment useful in connection with the present invention;

DETAILED DESCRIPTION OF THE INVENTION

Figure 1:
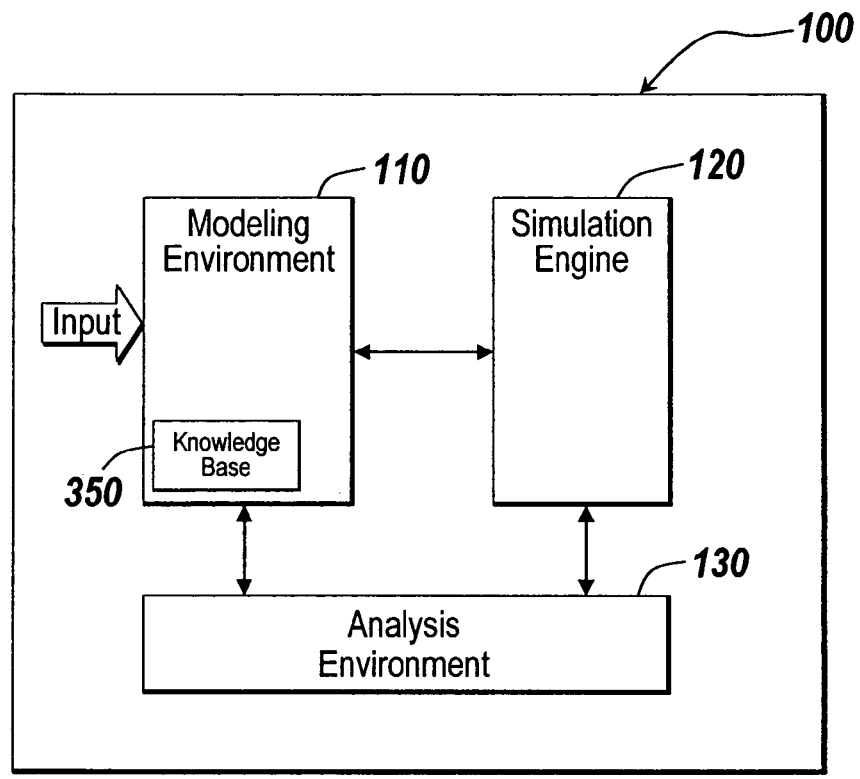
FIG. 1 is a block diagram of one embodiment of an integrated modeling, simulation and analysis environment.

Referring now to FIG. 1, a high-level block diagram of one embodiment of an integrated system for modeling, simulating, and analyzing chemical reactions and biological systems that include biological processes 100 is shown. As shown in FIG. 1, the system 100 includes a modeling component designated as a modeling environment 110 in the exemplary depiction of FIG. 1, a simulation engine 120, and an analysis environment 130. The simulation engine 120 communicates with the modeling environment 110. The simulation engine 120 receives models of chemical reactions or biological processes generated using the modeling environment 110. The simulation engine 120 communicates refinements to models created in the modeling environment 110. The analysis environment 130 is in communication with both the modeling environment 110 and the simulation engine 120. The analysis environment 130 may be used to perform various types of analysis directly on models created in the modeling environment 110. Also, the analysis environment 130 may receive and process results from the simulation engine 120 representing the execution by the simulation engine 120 of a model produced in the modeling environment. In other words, the simulation engine 120 generates the dynamic behavior of the model and communicates at least some of this dynamic behavior to the analysis environment. The analysis environment 130 may provide refinements to a model in the modeling environment 110 and may provide parameters for use by the simulation engine 120 when executing a model. The interaction between the modeling environment 110, the simulation engine 120, and the analysis environment 130 will be discussed in more detail below.

Figure 2A:
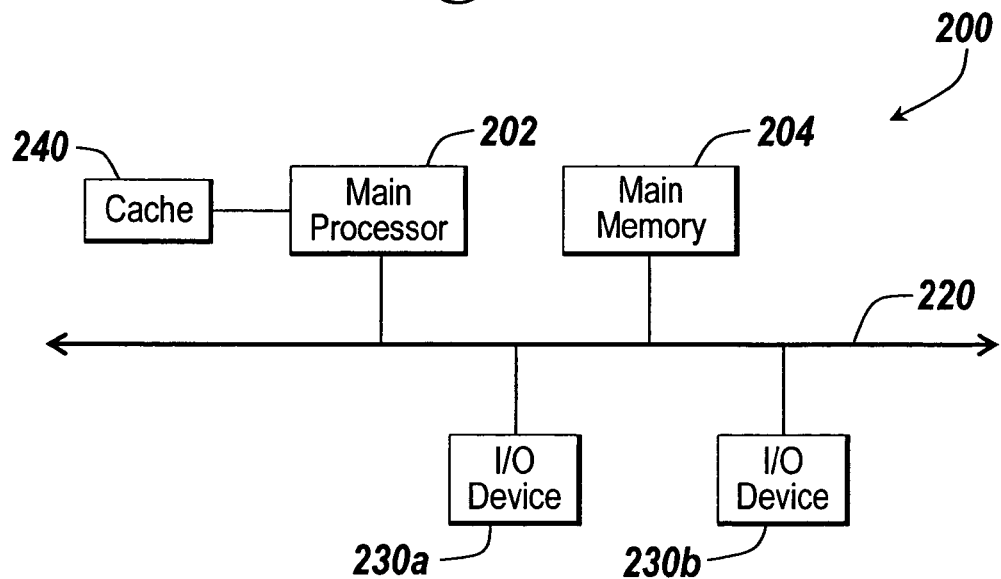
FIG. 2A is a block diagram of one embodiment of personal computer useful in connection with the present invention.
Figure 2B:
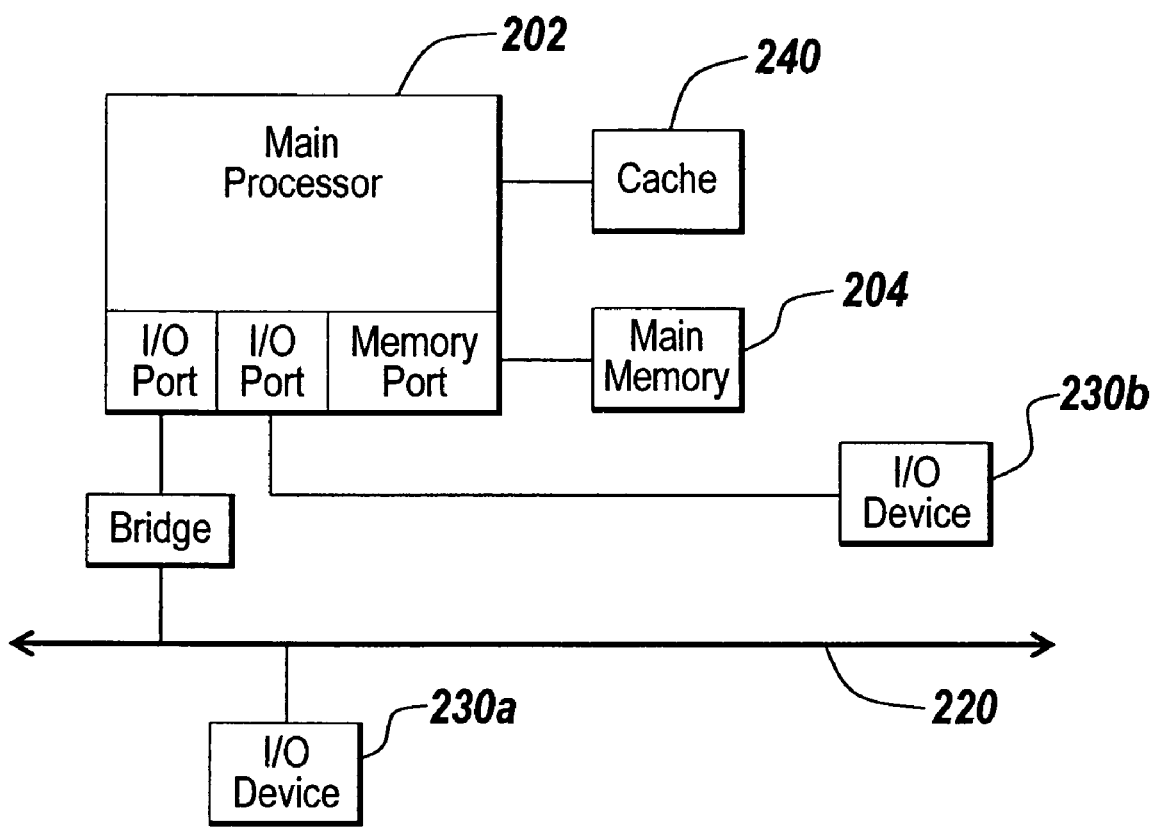
FIG. 2B is a block diagram of another embodiment of a personal computer useful in connection with the present invention.

The integrated system depicted in FIG. 1 may execute on a number of different computing platforms, such as supercomputers, mainframe computers, minicomputers, clustered computing platforms, workstations, general-purpose desktop computers, laptops, and personal digital assistants. FIGS. 2A and 2B depict block diagrams of typical general-purpose desktop computers 200 useful in the present invention. As shown in FIGS. 2A and 2B, each computer 200 includes a central processing unit 202, and a main memory unit 204. Each computer 200 may also include other optional elements, such as one or more input/output devices 230a-230b (generally referred to using reference numeral 230), and a cache memory 240 in communication with the central processing unit 202.

The central processing unit 202 is any logic circuitry that responds to and processes instructions fetched from the main memory unit 204. In many embodiments, the central processing unit is provided by a microprocessor unit, such as: the 8088, the 80286, the 80386, the 80486, the Pentium, Pentium Pro, the Pentium II, the Celeron, or the Xeon processor, all of which are manufactured by Intel Corporation of Mountain View, Calif.; the 68000, the 68010, the 68020, the 68030, the 68040, the PowerPC 601, the PowerPC604, the PowerPC604e, the MPC603e, the MPC603ei, the MPC603ev, the MPC603r, the MPC603p, the MPC500, the MPC740, the MPC745, the MPC750, the MPC755, the MPC 5500, the MPC7400, the MPC7410, the MPC7441, the MPC7445, the MPC7447, the MPC7450, the MPC7451, the MPC7455, the MPC7457 processor, all of which are manufactured by Motorola Corporation of Schaumburg, Ill.; the Crusoe TM5800, the Crusoe TM5600, the Crusoe TM5500, the Crusoe TM5400, the Efficeon TM8600, the Efficeon TM8300, or the Efficeon TM8620 processor, manufactured by Transmeta Corporation of Santa Clara, Calif.; the RS/6000 processor, the RS64, the RS 64 II, the P2SC, the POWER3, the RS64 III, the POWER3-II, the RS 64 IV, the POWER4, the POWER4+, the POWER5, or the POWER6 processor, all of which are manufactured by International Business Machines of White Plains, N.Y.; or the AMD Opteron, the AMD Athlon 64 FX, the AMD Athlon, or the AMD Duron processor, manufactured by Advanced Micro Devices of Sunnyvale, Calif.

Main memory unit 204 may be one or more memory chips capable of storing data and allowing any storage location to be directly accessed by the microprocessor 202, such as Static random access memory (SRAM), Burst SRAM or Synch-Burst SRAM (BSRAM), Dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDEC SRAM, PC100 SDRAM, Double Data Rate SDRAM (DDR SDRAM), Enhanced SDRAM (ESDRAM), SyncLink DRAM (SLDRAM), Direct Rambus DRAM (DRDRAM), or Ferroelectric RAM (FRAM). In the embodiment shown in FIG. 2A, the processor 202 communicates with main memory 204 via a system bus 220 (described in more detail below). FIG. 2B depicts an embodiment of a computer system 200 in which the processor communicates directly with main memory 204 via a memory port. For example, in FIG. 2B the main memory 204 may be DRDRAM.

FIGS. 2A and 2B depict embodiments in which the main processor 202 communicates directly with cache memory 240 via a secondary bus, sometimes referred to as a "backside" bus. In other embodiments, the main processor 202 communicates with cache memory 240 using the system bus 220. Cache memory 240 typically has a faster response time than main memory 204 and is typically provided by SRAM, BSRAM, or EDRAM.

In the embodiment shown in FIG. 2A, the processor 202 communicates with various I/O devices 230 via a local system bus 220. Various busses may be used to connect the central processing unit 202 to the I/O devices 230, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display, the processor 202 may use an Advanced Graphics Port (AGP) to communicate with the display. FIG. 2B depicts an embodiment of a computer system 200 in which the main processor 202 communicates directly with I/O device 230*b* via HyperTransport, Rapid I/O, or InfiniBand. FIG. 2B also depicts an embodiment in which local busses and direct communication are mixed: the processor 202 communicates with I/O device 230*a* using a local interconnect bus while communicating with I/O device 230*b* directly.

A wide variety of I/O devices 230 may be present in the computer system 200. Input devices include keyboards, mice, trackpads, trackballs, microphones, and drawing tablets. Output devices include video displays, speakers, inkjet printers, laser printers, and dye-sublimation printers. An I/O device may also provide mass storage for the computer system 200 such as a hard disk drive, a floppy disk drive for receiving floppy disks such as 3.5-inch, 5.25-inch disks or ZIP disks, a CD-ROM drive, a CD-R/RW drive, a DVD-ROM drive, tape drives of various formats, and USB storage devices such as the USB Flash Drive line of devices manufactured by Twintech Industry, Inc. of Los Alamitos, Calif.

In further embodiments, an I/O device 230 may be a bridge between the system bus 220 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a Fibre-Channel bus, or a Serial Attached small computer system interface bus.

General-purpose desktop computers of the sort depicted in FIGS. 2A and 2B typically operate under the control of operating systems, which control scheduling of tasks and access to system resources. Typical operating systems include: MICROSOFT WINDOWS, manufactured by Microsoft Corp. of Redmond, Wash.; MacOS, manufactured by Apple Computer of Cupertino, Calif.; OS/2, manufactured by International Business Machines of Armonk, N.Y.; and Linux, a freely-available operating system distributed by Caldera Corp. of Salt Lake City, Utah, among others.

In still other embodiments the computers may operate under the control of real-time operating systems such as AMX, KwikNet, KwikPeg (all manufactured by KADAK Products Ltd.), C EXECUTIVE (manufactured by JMI Software Systems, Inc.), CMX-RTX (manufactured by CMX Systems, Inc.), DeltaOS (manufactured by CoreTek Systems, Inc.), eCos (manufactured by Red Hat, Inc.), embOS (manufactured by SEGGER Microcontroller Systeme GmbH), eRTOS (manufactured by JK Microsystems, Inc.), ETS (manufactured by VenturCom), EYRX (manufactured by Eyring Corporation), INTEGRITY (manufactured by Green Hills Software, Inc.), INtime® real time extension to Windows® (manufactured by TenAsys Corporation), IRIX (manufactured by SGI), iRMX (manufactured by TenAsys Corporation), Jbed (manufactured by esmertec, inc.), LynxOS (manufactured by LynuxWorks), MQX (manufactured by Precise Software Technologies Inc), Nucleus PLUS (Accelerated Technology, ESD Mentor Graphics), On Time RTOS-32 (manufactured by On Time Informatik GmbH), OS-9 (manufactured by Microware Systems Corporation), OSE (manufactured by OSE Systems), PDOS (manufactured by Eyring Corporation), PSX (manufactured by JMI Software Systems, Inc.), QNX Neutrino (manufactured by QNX Software Systems Ltd.), QNX4 (manufactured by QNX Software Systems Ltd.), REDICE-Linux (manufactured by REDSonic, Inc.), RTLinux (manufactured by Finite State Machine Labs, Inc.), RTX 5.0 (manufactured by VenturCom), Portos (manufactured by Rabih Chrabieh), smx (manufactured by Micro Digital, Inc.), SuperTask! (manufactured by U S Software), ThreadX (manufactured by Express Logic, Inc.), Treck AMX (manufactured by Elmic Systems USA, Inc.), Treck MicroC/OS-II (manufactured by Elmic Systems USA, Inc.), TronTask! (manufactured by U S Software), TTPos: (manufactured by TTTech Computertechnik AG), Virtuoso (manufactured by Eonic Systems), VxWorks 5.4 (manufactured by Wind River), SCORE, DACS and TADS (all manufactured by DDC-I), Nimble—the SoC RTOS (manufactured by Eddy Solutions), Nucleus (manufactured by Accelerated Technology), or Fusion RTOS (manufactured by DSP OS, Inc.). In these embodiments the central processing unit 202 may be replaced by an embedded processor, such as the Hitachi SH7000, manufactured by Kabushiki Kaisha Hitachi Seisakusho, of Tokyo, Japan or the NEC V800, manufactured by NEC Corporation of Tokyo, Japan.

Referring back to FIG. 1, and in more detail, the modeling environment 110 accepts input to create a model of the chemical or biochemical reaction to be simulated. In some embodiments, the modeling environment 110 accepts input contained in a file, such as a file in Systems Biology Markup Language (SBML). In others of these embodiments, the file may be in HyperText Markup Language (HTML) format, Extensible Markup Language (XML) format, a proprietary markup language, or a text file in which fields are delimited by tabs or commas. Alternatively, the modeling environment 110 may accept input produced by a user via either a command-line interface or a graphical user interface.

Figure 3A:
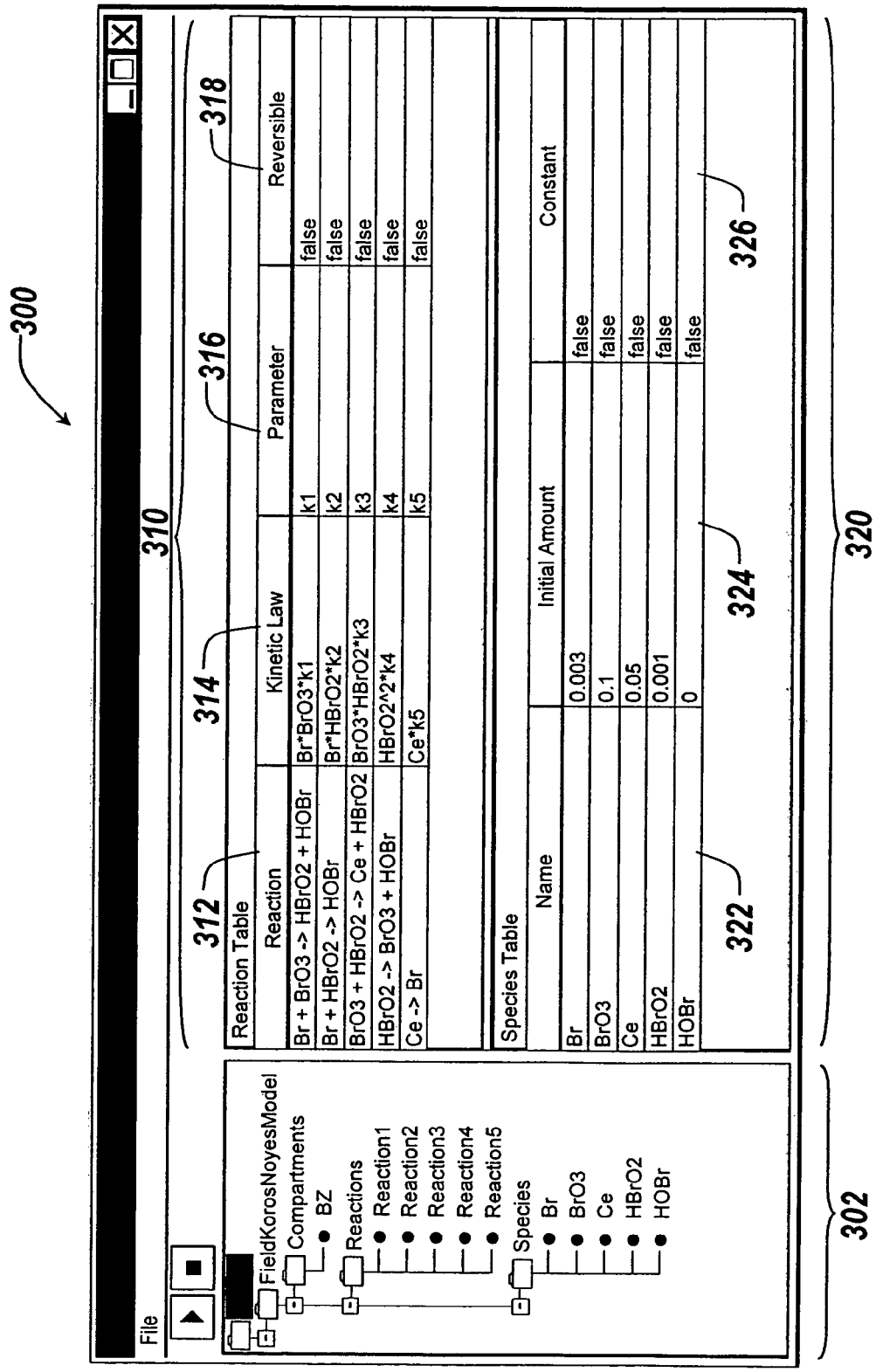
Figure 3B:
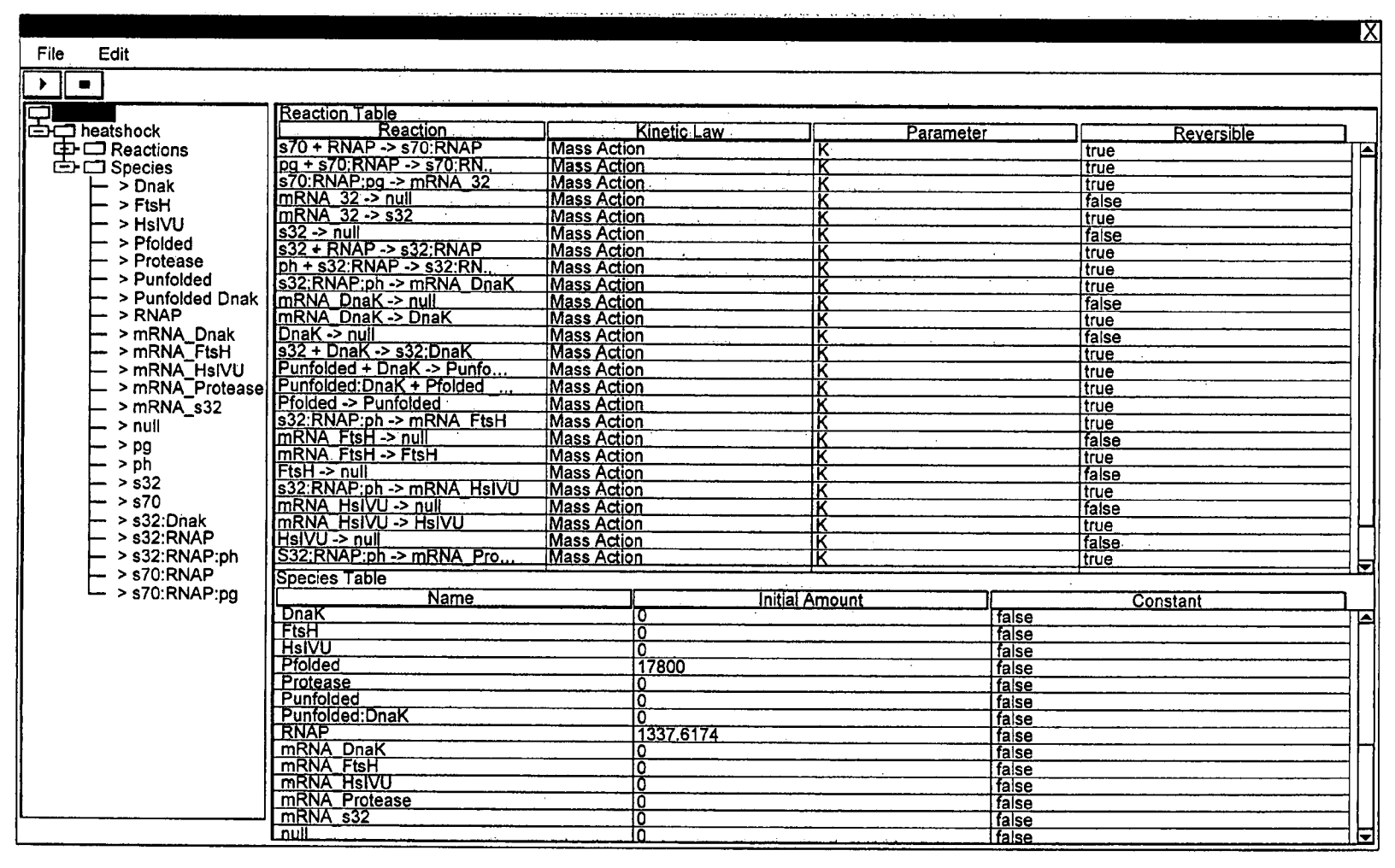

FIGS. 3A and 3B depicts an embodiment of a tabular graphical user interface 300 that may be used to receive input manufactured by a user for creating a model. As shown in FIGS. 3A and 3B, the user interface may include a model pane 302. In the embodiment shown in FIGS. 3A and 3B, the model pane 302 lists one or more models in a tree structure familiar to users of computers operating under control of the WINDOWS operating system, manufactured by Microsoft Corp. of Redmond, Wash. In the particular embodiment depicted by FIG. 3A, a single model of a chemical reaction is contained in the model pane 302, indicated by the folder labeled "FieldKorosNoyesModel". That model contains three subfolders: "Compartments"; "Reactions"; and "Species". The subfolders represent pieces of the modeled reaction. Other graphical user interface schemes may be used to present this information to the user of a system 100. In some embodiments, the model pane 302 may display a number of folders representing models. User selection of a particular folder causes the system to display folder in the model pane 302 that represent pieces of the reaction, e.g., compartments, reactions, and species. In still other embodiments, each model and all components of all models may be displayed in the model pane 302 and each model may be associated with a "radio button," Selection of the radio button associates with a model causes that model and its constituents to be actively displayed. In some of these embodiments, unselected models are displayed in grey type, or may have a transparent grey overlay indicating that they are not currently the active model.

Referring back to FIG. 3A, the graphical user interface 300 also includes a reaction table 310, and a species table 320. The reaction table 310 is associates with the "Reactions" folder displayed in the model pane 302. Similarly, the species table 320 is associated with the "Species" folder displayed in the model pane 302. In some embodiments, collapsing the associated folder causes the table to not be displayed. The respective tables may be displayed in their own graphical user interface window, rather than in the same window as the graphical user interface 300, as shown in FIG. 3A.

The reaction table 310 lists each reaction present in a modeled biological process or chemical reaction. In the embodiment shown in FIG. 3A, the modeling environment 300 displays reactions present in the Field-Koros-Noyes model of the Belousov-Zhabotinsky reaction and includes four columns: a reaction column 312, a kinetic law column 314, a parameter column 316, and a reversible column 318. Each row of the reaction table 310 corresponds to a particular reaction. The number and format of columns displayed by the reaction table may be selected by the user. In other embodiments, the modeling environment 110 may select the number and format of columns to display based on the type of reaction selected by the user.

Referring back to the embodiment shown in FIG. 3A, the reaction column 312 displays a reaction represented in an abstract format, e.g., Ce→Br. In other embodiments, the reaction may be represented as a differential equation, in stochastic format, or as a hybrid of two or more of these formats. In some embodiments, the reaction table includes a column identifying modifiers of the reaction. For example, some reactions can be catalyzed by a substance. This may be represented in the tabular format as Ce-m(s)→Br, meaning that the presence of "s" causes Ce to convert into Br.

In the embodiment shown in FIG. 3A, the reaction table 310 also includes a kinetic law column 314 which identifies the kinetic law expression the identified reaction follows. In the embodiment shown in FIG. 3A, the kinetic law associated with the Ce→Br reaction is "Ce*k5," meaning that Ce is consumed at a rate controlled by the parameter "k5" and the amount of Ce present. In the embodiment shown in FIG. 3A, the parameters for the kinetic law expression are listed in the parameter column 316. In some embodiments, the reaction table 310 includes a column identifying the name of the kinetic law associated with a particular reaction, e.g. "mass action" or "Michaels-Menten." In other embodiments, the reaction table 310 includes a column identifying the units in which the kinetic law parameters are expressed, e.g., 1/seconds, 1/(moles*seconds), etc.

Still referring to the embodiment shown in FIG. 3A, the reaction table 310 includes a reversible column 318, which indicates whether the associated reaction is reversible. A reversible reaction is one which occurs in either direction, i.e. Ce<—>Br. In some embodiments the reaction table 310 may include a column identifying dynamics of the reaction, e.g., "fast" or "slow." In some of these embodiments, the rapidity with which a reaction occurs is identified on a scale of 1 to 10. In still other embodiments, the user may be presented with a slide control that allows the rapidity of various reactions to be set relative to one another. In still further embodiments, the reaction table 310 may include a column for annotations or notes relating to the reaction.

The modeling environment 300 shown in FIG. 3A also displays a species table 320. In the embodiment shown in FIG. 3, the species table 320 includes a name column 322, an initial amount column 324, and a constant column 326. The species table depicts the initial conditions and amounts of material used in the modeled biological process or chemical reaction. Thus, in the embodiment shown in FIG. 3, the modeled biological process begins with 0.003 molar units of bromine, i.e., 0.003 multiplied by Avrogado's number. The constant column 326 is set to "true" if the model should assume that there is an infinite supply of a particular species. In other embodiments the species table 320 includes other columns such as a column identifying units (e.g., moles, molecules, liters, etc.), whether a particular species is an independent variable in the model (i.e., whether the species is an input to the system), a column for annotations, or a column for notes.

In some embodiments, the modeling environment 300 accepts as input a file in a markup language and converts that file into a graphical display of the sort depicted in FIG. 3A. For example, one representation of the Field-Koros-Noyes model of the Belousov-Zhabotinsky reaction in markup language that corresponds to the particular embodiment shown in FIG. 3A is shown in Appendix A to this document.

For example, a process may be provided that uses the information embedded in the tags of the markup language file, e.g., <reaction name="Reaction5" reversible="false">, to generate the tabular form of the model shown in FIGS. 3A and 3B. In some of these embodiments, a web browser may be modified to parse files containing models written in markup language in order to create the tabular form of the model shown in FIGS. 3A and 3B. In other embodiments, a process may accept the model as input and generate as output code that is directly executable on a processor, such a code written in the C programming language.

Conversion of a model into executable code allows the executable code to be transmitted to multiple computers via a network for execution on those computers. In these embodiments computers may be connected via a number of network topologies including bus, star, or ring topologies. The network can be a local area network (LAN), a metropolitan area network (MAN), or a wide area network (WAN) such as the Internet. And the respective computers may connect to the network 180 through a variety of connections including standard telephone lines, LAN or WAN links (e.g., T1, T3, 56 kb, X.25), broadband connections (ISDN, Frame Relay, ATM), and wireless connections. Connections can be established using a variety of communication protocols (e.g., TCP/IP, IPX, SPX, NetBIOS, NetBEUI, SMB, Ethernet, ARCNET, Fiber Distributed Data Interface (FDDI), RS232, IEEE 802.11, IEEE 802.11a, IEEE 802.11b, IEEE 802.11g and direct asynchronous connections).

In these embodiments, a master server parses a model written in markup language. The model may be retrieved from a hard disk or from another computer accessed via a network connection. In other embodiments the model is input by a user using a tabular user input such as the one shown in FIGS. 3A and 3B or a graphical user interface such as the one shown in FIG. 4. The master server parses the model to produce executable code. The executable code produced by the master server may be compiled code, such as code written in C, C+, C++, or C# and compiled to run on a target platform or the executable code produced by the master server may be a in a bytecode language such as JAVA. In some embodiments the executable code is transmitted to one or more computers via a network connection. The one or more computers execute the code representing the model and return the generated result to the master server. The master server may store the retrieved results for later analysis. In some embodiments the master server displays a graphical representation of each of the received results. In one embodiment, this technique is used to conduct Monte Carlo type analysis. In certain of these embodiments, the master server may collect and display each data point received and display each data point graphically in real-time.

FIG. 3B depicts in tabular form reactions for simulating the *E. Coli* heat shock response model. As described above in connection with FIG. 3A, the upper table displays the various reactions involved in transcription and translation of the heat shock proteins as well as the interactions of heat shock proteins with unfolded (or denatured) proteins. As depicted in FIG. 3B, all reactions have mass action kinetics and some are reversible, while some are not. Another method of representing chemical or biochemical reactions is by way of a block diagram.

Figure 4:
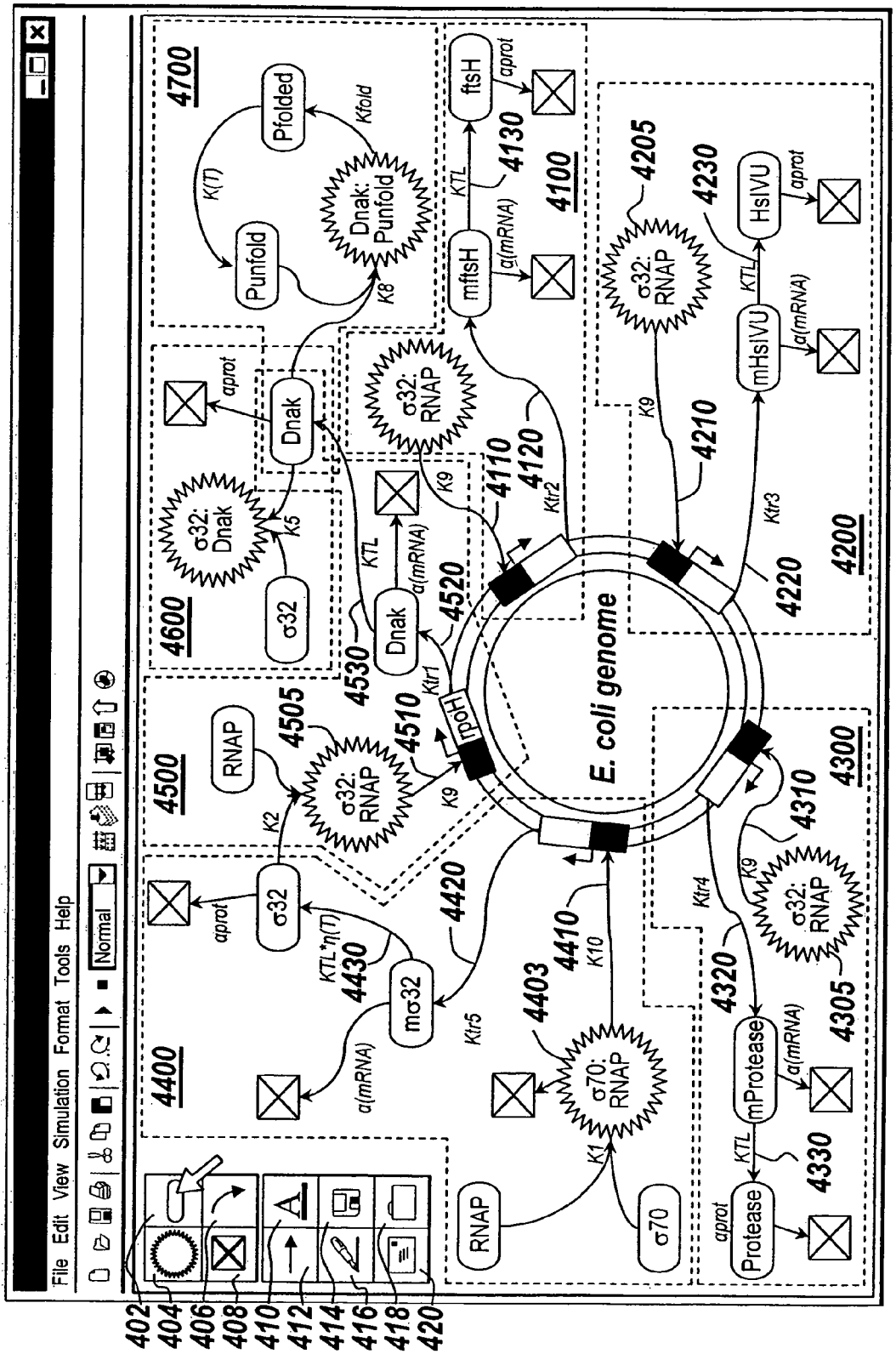
FIG. 4 is a screenshot of one embodiment of a graphical user interface that facilitates construction of block diagram representations of chemical reactions or biological processes.

In still other embodiments, the modeling environment 300 allows a user to represent a biological process or chemical reaction as a block diagram. FIG. 4 depicts an embodiment of a block diagram modeling environment. In the embodiment depicted in FIG. 4, a block diagram showing heat shock reaction in E. Coli bacteria is under construction. As is well known, heat shock response in E. coli is a protective cellular response to heat induced stress. Elevated temperatures result in decreased E. coli growth, in large part, from protein unfolding or misfolding. The heat shock response, via heat shock proteins, responds to heat induced stress by refolding proteins via chaperones or by degrading nonfunctional proteins via proteases.

The block diagram shown in FIG. 4 depicts the expression of five particular gene sequences involved in the heat shock response. In part, FIG. 4 depicts pathways 4100, 4200, 4300 for the expression of proteases involved in beat shock response. Pathways 4100, 4200, 4300 represent the expression of heat shock proteins ftsH, Hs1VU and other proteases, respectively. The pathways 4100, 4200, 4300 are activated by the interaction 4105, 4205, 4305 of $\sigma^{32}$ with RNA polymerase at the promoter of the respective sequence. Each pathway 4100, 4200, 4300 depicts the transcription 4120, 4220, 4320 of the mRNA mediated 4110, 4210, 4310 by the $\sigma^{32}$ and RNA polymerase interaction 4105, 4205, 4305 at the promoter and the subsequent translation 4130, 4230, 4330 of the protease. The heat shock proteases, including ftsH and Hs1VU, serve to degrade proteins rendered nonfunctional by heat stress. Similarly, the diagram depicts the pathways 4400, 4500 involved in the expression of the heat shock proteins $\sigma^{70}$ and DnaK, respectively. The expression of the $\sigma^{32}$ protein is activated 4410 by the interaction 4403 of $\sigma^{70}$ and RNA polymerase at the promoter. The $\sigma^{32}$ mRNA is transcribed 4420 and, subsequently, $\sigma^{32}$ is translated 4430. In a closely related pathway 4500, the heat shock protein DnaK is translated. The interaction 4505 of $\sigma^{32}$ and RNA polymerase at the promoter activate 4510 the transcription 4520 of DnaK mRNA and, subsequently, the translation 4530 of DnaK. DnaK, in turn, may either interact 4600 with $\sigma^{32}$ so as to stabilize $\sigma^{32}$ or, alternatively, may refold 4700 the proteins unfolded by heat stress.

A block diagram editor allows users to perform such actions as draw, edit, annotate, save, and print out block diagram representations of dynamic systems. Blocks are the fundamental mathematical elements of a classic block diagram model. In some of these embodiments, the modeling environment includes two classes of blocks, non-virtual blocks and virtual blocks. Non-virtual blocks are elementary dynamic systems, such as the $\sigma^{32}$ and RNA polymerase interaction 4105, 4205, 4305. A virtual block may be provided for graphical organizational convenience and plays no role in the definition of the system of equations described by the block diagram model. For example, in the block diagram of the heat shock mechanism in E. Coli bacteria depicted in FIG. 4, gene transcription mediated by $\sigma^{32}$ to produce proteins, represented by 4100, 4200, and 4300, may be represented as a single, virtual block. Hierarchical modeling (such as the use of subsystems) may be used to improve the readability of models.

In some embodiments, the meaning of a non-virtual block may be extended to include other semantics, such as a "merge" block semantic. The merge block semantic is such that on a given time step its output is equal to the last block to write to an input of the merge block. In tabular graphical user interface embodiments, a merge block may be combined with "wild card" characters to expand a single table entry into multiple instances of a reaction. For example, the reaction:

*transcription_factor:RNAP –> gene –> mRNA –> protein which uses *transcription_factor as a "wild card," allowing multiple protein expressions to be identified in a model using a single line reaction. In general, any regular expression may be used to signal the existence of a "wild card." Regular expressions, and the techniques used to compile a regular expression into multiple instances of code, are well-known. The transcription factors to be used by the model may be provided from a database query, a file, or by user input at the time the reaction is expanded to generate the executable model. Each transcription factor that is provided results in a different reaction that, potentially, causes a different gene to produce messenger RNA and express a particular protein. This technique may be used to produce sets of reactions with minimal input on the user's part.

In still other embodiments, the modeling environment 300 may also provide for conditional execution, which is the concept of conditional and iterative subsystems that control when in time block methods execute for a sub-section of the overall block diagram.

The block diagram editor is a graphical user interface (GUI) component that allows drafting of block diagram models by a user. FIG. 4 depicts an embodiment of a GUI for a block diagram editor that features a floating element palette. In the embodiment shown in FIG. 4, the GUI tools include various block tools 402, 404, 408, various wiring line connection tools 406, 412, an annotation tool 416, formatting tool 410, a save/load tool 414, a notification tool 420 and a publishing tool 418. The block tools 402, 404, 408 represent a library of all the pre-defined blocks available to the user when building the block diagram. Individual users may be able to customize this palette to: (a) reorganize blocks in some custom format, (b) delete blocks they do not use, and (c) add custom blocks they have designed. The blocks may be dragged through some human-machine interface (such as a mouse or keyboard) on to the window (i.e., model canvas). The graphical version of the block that is rendered on the canvas is called the icon for the block. There may be different embodiments for the block palette including a tree-based browser view of all of the blocks. In these embodiments, the floating element palette allows a user to drag block diagram elements from a palette and drop it in place on the screen. In some of these embodiments there may also be a textual interface with a set of commands that allow interaction with the graphical editor. For example, dragging a polymerase block to the model may cause the system to prompt the user for the protein to be used in the polymerase reaction.

Using this textual interface, users may write special scripts that perform automatic editing operations on the block diagram. A user generally interacts with a set of windows that act as canvases for the model. There can be more than one window for a model because models may be partitioned into multiple hierarchical levels through the use of subsystems (discussed further below). In still other embodiments, only a textual interface may be provided for facilitating the user's construction of the block diagram.

The wiring line connection tools 406, 412 allow users to draw directed lines that connect the blocks in the model's window. In some embodiments a single wiring line tool is provided and the user connects blocks by selecting the tool, selecting a start point, and selecting the end point. In other embodiments, multiple connection tools may be present (such as the embodiment depicted in FIG. 4). Connections may be added through various other mechanisms involving human-machine interfaces such as the keyboard. The modeling environment 300 may also provide various forms of auto-connection tools that connect blocks automatically on user request to produce an aesthetically pleasing layout of the block diagram (especially those with high complexity with large numbers of blocks). Connection of one block to another signifies that the species represented by the first block, or the output of that block if it represents a transaction, is an input to the second block.

The annotation tool 416 allows users to add notes and annotations to various parts of the block diagram. The annotations may appear in a notes or annotation column when the model is viewed in a tabular format. When viewed in graphical format, the notes may appear close to annotated block or they may be hidden.

The formatting tool 410 enables users to perform various formatting operations that are generally available on any document editing tool. These operations help pick and modify the various graphical attributes of the block diagram (and constituent blocks) such as include font-selection, alignment & justification, color selection, etc. The block diagram and all the blocks within the block diagram generally have a set of functional attributes that are relevant for the execution or code-generation. The attribute editing tool provides GUIs that allows these attributes to be specified and edited.

The save/load tool 414 allows a created block diagram model to be saved. The saved model can be reopened in the editor at some later juncture through a load mechanism. Users may save blocks including pre-constructed subsystems into a separate class of block-diagrams called libraries. Such libraries facilitate reuse of the same block in a number of other block-diagrams. The load/save mechanism is specially equipped to handle loading and saving of blocks in a block-diagram that actually reside in libraries.

A publishing tool 418 may be provided to enable the viewing of the block diagram as a document that can be published in any standard document formats (examples: PostScript, PDF, HTML, SBML, XML, SGML, SBML etc.). Those skilled in the art will recognize that, the windows for multiple models and all of the tools mentioned above could potentially be embedded in a single Multi-Document Interface (MDI) for providing a unified software environment.

A notification tool 420 allows a user working on a block diagram to send a message to another user. In some embodiments, the notification tool 420 causes the current version of the block diagram, to be mailed to the specified user.

Those skilled in the art will also recognize that block-diagram packages offer scripting languages for writing out programs that automatically carry out a series of operations that would normally require interaction with the GUI, such as block addition, block deletion, starting and terminating execution, or modifying block attributes, etc.

The modeling environment 300 may also offer a variety of other GUI tools that improve the ability of users to build and manage large block diagrams. Examples of such GUIs include: (a) a Finder that helps find various objects such as blocks and lines within a block-diagram, (b) a Debugger that helps debug the execution of block-diagrams, (c) a Revision Control UI for managing multiple revisions of the block-diagram, and (d) a Profiler for viewing timing results while executing a block-diagram.

A typical base data-structure for a block may be represented as:

```
class Block {
    public:
        // Access methods for setting/getting block data
        ...
        // Methods for block editing
        virtual ErrorStatus BlockDrawIcon( );
        virtual BlockParameterData BlockGetParameterData( );
        ...
        // Methods for block compilation
        ...
        // Methods for block execution
        ...........................................
        virtual ErrorStatus BlockOutput( ) = 0;
        virtual ErrorStatus BlockDerivative( ) = 0;
        virtual ErrorStatus BlockUpdate( ) = 0;
        ...
    private:
        BlockGraphicalData blkGraphicalAttributes;
        BlockFunctionalData blkFunctionalAttributes;
        BlockCompiledData blkCompiledAttributes;
        BlockExecutionData blkExecutionData;
        ...
};
```

Although the example of the data structure above is written in C++, those skilled in the art will recognize that equivalent data structures written in other languages may also be used. The major data fields of the block data structure fall into four categories, a graphical attributes field, a functional attributes field, a compiled attributes field and an execution data field.

The graphical attributes field is responsible for storing information relevant for graphical rendering of the block within its parent block diagram's GUI. Attributes specific to the block icon such as font, color, name, and icon-image are stored in this field. It should be noted that modifying these attributes does not affect the dynamics of the model using this block. The functional attributes field is responsible for specifying block attributes that may potentially affect the dynamics of the model using this block. These attributes are specified for the block as a whole and the input and output ports of the block. Examples of block attributes include block sample times and restrictive flags. Block sample times specify if the block corresponds to an elemental, continuous, discrete, or hybrid dynamic system. If the block is an elemental discrete-time system, then the attribute specifies the spacing between time instants at which the block response should be traced. A restrictive flag disallows the use of blocks in certain modeling contexts. For example, one may impose the restriction that there may only be one instance of given block in a model.

Attributes of block ports specify properties of the data that is either available or produced at that port. Block port attributes include dimensions, datatypes, sample rates, and direct feedthrough. Dimension attributes are individual dimensions of a multi-dimensional matrix that is used as a container for data elements. Datatype attributes are the datatype of each element of data in the data container. A complexity attribute is a flag to specify if each data element is real or complex. A sample rate attribute specifies how when the signal corresponding to an input or output port will be used. The port sample times may sometimes be used to implicitly infer the block's sample time. The direct feedthrough attribute is specified only for input ports and indicates whether or not the Output equations of the block are a function of the given input. This attribute helps in determining the sequence in which block methods should be executed while executing the block diagram.

The compiled attributes field of the block data structure holds the attributes of the block and its ports that mirror the functional attributes listed above. This field is filled in during block diagram compilation by utilizing the functional attributes of the block in conjunction with the functional and compiled attributes of the blocks that are connected to it. This process of determining the compiled attributes manufactured by the functional attributes is termed attribute propagation. Attribute propagation is described in greater detail below in the section on block diagram compilation. The execution data field is mainly responsible for storing the memory locations that are going to serve as sources for block inputs, outputs, states, parameters, and other work areas during execution of blocks.

The block data structure also has a set of associated methods that may be categorized as access methods to data fields, methods used in editing, methods used in compilation and methods used in execution. Access methods to data fields help in setting and getting the various data fields of the block. Methods used in editing are called by the block diagram editor in order to render the block appropriately in the GUI of its parent block diagram. For instance, this set of methods may include a BlockDrawIcon method that determines the shape the block icon has on the GUI. Methods used in compilation are methods that are called by the block diagram compilation engine. They help validate the connections of the block to other blocks on the block diagram. The methods used in execution include a number of different run-time methods that are required for execution. These include the BlockOutput, BlockUpdate, BlockDerivative methods that realize the Output, Update, and Derivative equations discussed earlier in the context of dynamic systems. In addition to these methods several other run-time methods may be provided, such as the Jacobian, Projection, ZeroCrossings, Enable, Disable, Initialize, EvalParams (check and process parameters), and GetTimeOfNextHit methods. It should be noted that there is no explicit method for algebraic equations because these are represented and processed in a different manner which will be discussed below in connection with the discussion of the simulation engine 120.

In some embodiments, the modeling environment 110 includes a knowledge base 350 that aids construction of a model. In some of these embodiments, the knowledge base 350 contains models for various reactions, e.g. glycolysis. In these embodiments, when a user begins to input reactions consistent with a model for glycolysis, the knowledge base 350 may enter the remaining reactions for the user. Alternatively, the knowledge base 350 may offer different models of the reaction to the user. In some of these embodiments, the offered models represent the target reaction with varying levels of detail. In other embodiments, the knowledge base 350 may insert parameters or indications of reversibility for entered reactions. The knowledge base 350 may also provide assistance to a user inputting a block diagram representation of a chemical or biochemical reaction. For example, the knowledge base 350 may prevent a user manufactured by connecting blocks inconsistent with the modeled reaction. Examples of publicly-available databases that may be used to facilitate generation of models include the Swissprot database, National Center for Biotechnology Information (NCBI) database, the Protein Data Bank, and Kyoto Encyclopedia of Genes and Genomes (KEGG). Alternatively, the user may provide private databases to act as a knowledge base 350 for facilitating creation of models.

Blocks in a block diagram may be virtual or non-virtual. The designation of a block as non-virtual indicates that it influence the equations in the mathematical model for the dynamic system. In the context of block diagram software, it is beneficial to include other virtual blocks that do not affect the equations in the dynamic system's model. Such blocks help improve the readability and modularity of the block diagram and wield no semantic influence on the mathematical model. Examples of such virtual blocks include virtual subsystems, inport blocks and outport blocks, bus creator blocks and From and Goto blocks.

Modularity may be achieved in a block diagram by layering the block diagram through the use of subsystems. A subsystem facilitates layering by allowing a collection of blocks to be represented by a single block with input and output signals. The input and output signals of the subsystem are accessible to the constituent blocks within the subsystem. A subsystem is a virtual subsystem if its constituent blocks are moved back into the main block diagram model during the model's execution. Within a virtual subsystem graphical entities, called inport and outport blocks, are provided to define signal connections to the parent block diagram. These inport and outport blocks indicate a tunnel-through signal connection to the parent block diagram.

As noted previously, to facilitate modeling fairly large and complex dynamic systems, users may be allowed to layer block diagrams. A subsystem facilitates such layering by allowing a collection of blocks to be represented by a single block with input and output signals. The input and output signals of the subsystem are accessible to its constituent blocks. By nesting subsystems within each other, one can create block diagrams with arbitrary layers of hierarchy. Ideally a subsystem has no impact on the meaning of the block diagram. Additionally, subsystems provide a way of grouping blocks together and allowing other block diagram constructs to impose unified control on the constituent blocks. To enhance the modularity of subsystems, modeling software also allows aggregated list(s) of parameters of the blocks within the subsystem to be accessed from a single GUI, and defines and displays special icons on the subsystems. The process of defining the parameter list and the special icon is called masking a subsystem.

There are two main types of subsystem blocks, virtual subsystems and non-virtual subsystems. Virtual subsystems serve the purpose of providing the block diagram with a graphical hierarchy. Non-virtual subsystems behave like an elemental dynamic system with its own execution methods (Output, Update, Derivatives, etc.). These execution methods in turn call the execution methods of the constituent blocks. The classes of non-virtual subsystems are:

Atomic subsystems. These are similar to virtual subsystems, with the advantage of grouping functional aspects of models at a given layer. This is useful in modular design.

Conditionally-executed subsystems. These are non-virtual subsystems that execute only when a precondition is fulfilled:

Enabled subsystems. These are similar to Atomic subsystems, except that the constituent blocks only execute when an enable signal feeding the subsystem is greater than zero.

Triggered subsystems. These are similar to Atomic subsystems, except that the constituent blocks only execute when a rising and/or falling signal is seen on a triggering signal feeding the subsystem.

Enable with Trigger subsystems. These are an intersection of the properties of Enabled and Triggered subsystems.

Action subsystems. These subsystems are connected to action-initiator (e.g., an "If" or "SwitchCase" block), a block that explicitly commands the subsystem contents to execute. These subsystems are similar to Enabled subsystems except that the management of the "enabling" signal has been delegated to an action-initiator. Action subsystems define a new type of signal, called an action signal that signifies which subsystems are commanded to execute by the action-initiator.

Function-call subsystems. These subsystems provide a means of collecting blocks into a subsystem that is only executed when called by an owner block. The owner block may compute input signals for the subsystem before calling the subsystem. Additionally, the owner may also read output signals from the subsystem after calling it. Function-call subsystems define a new type of execution control signal, called a function-call signal that contains no data. It is used to define the execution relationship between the owner block and the function-call subsystem. Function-call owners may also designate themselves as an "interrupt" source. In simulation, they simulate the effects of an interrupt and in code generation they can attach themselves to an (asynchronous) interrupt.

While subsystems and For subsystems. These subsystems execute the constituent blocks multiple times on a given time step.

In other embodiments the knowledge base 350 may be used to facilitate further or broader understanding of the modeled reaction. For example, referring to the block diagram representation of the heat shock reaction in *E. Coli* bacteria, the knowledge base 350 can be used to identify other reactions in the heat shock reaction that use, or are impacted by, σ70. Alternatively, the knowledge base 350 may identify other reactions for *E. Coli* in which σ70 plays a part, e.g., chemotaxis. In this way, a broader understanding of the functioning of *E. Coli* in various environments can be achieved.

In still other embodiments the modeling environment 110 provides libraries from which blocks may be selected and included in a model. Models referenced by virtual or non-virtual blocks in a model, whether or not part of a library, are included in the model for execution. For embodiments in which executable code is generated, code representing the referenced models is also generated.

Virtual subsystems serve the purpose of providing the block diagram with a graphical hierarchy. Non-virtual subsystems behave like an elemental dynamic system with its own execution methods (Output, Update, Derivatives, etc.). These execution methods in turn call the execution methods of the constituent blocks.

Once a block diagram model has been constructed, model execution is carried out over a user-specified time span for a set of user-specified inputs. The execution begins when the block diagram is compiled. The compile stage marks the start of model execution and involves preparing data structures and evaluating parameters, configuring and propagating block characteristics, determining block connectivity, and performing block reduction and block insertion. The preparation of data structures and the evaluation of parameters create and initialize basic data-structures needed in the compile stage. For each of the blocks, a method forces the block to evaluate all of its parameters. This method is called for all blocks in the block diagram. If there are any unresolved parameters, execution errors are thrown at this point. During the configuration and propagation of block and port/signal characteristics, the compiled attributes (such as dimensions, data types, complexity, or sample time) of each block (and/or ports) are setup on the basis of the corresponding functional attributes and the attributes of blocks (and/or ports) that are connected to the given block through lines. The attribute setup is performed through a process during which block functional attributes "ripple through" the block diagram from one block to the next following signal connectivity. This process (referred to herein as "propagation"), serves two purposes. In the case of a block that has explicitly specified its block (or its ports') functional attributes, propagation helps ensure that the attributes of this block are compatible with the attributes of the blocks connected to it. If not, an error is issued. Secondly, in many cases blocks are implemented to be compatible with a wide range of attributes. Such blocks adapt their behavior in accordance with the attributes of the blocks connected to them. This is akin to the concept of polymorphism in object-oriented programming languages. The exact implementation of the block is chosen on the basis of the specific block diagram in which this block finds itself. Included within this step are other aspects such as validating that all rate-transitions within the model yield deterministic results and that the appropriate rate transition blocks are being used. The compilation step also determines actual block connectivity. Virtual blocks play no semantic role in the execution of a block diagram. In this step, the virtual blocks in the block diagram are optimized away (removed) and the remaining non-virtual blocks are reconnected to each other appropriately. This compiled version of the block diagram with actual block connections is used from this point forward in the execution process. The way in which blocks are interconnected in the block diagram does not necessarily define the order in which the equations (methods) corresponding to the individual blocks will be solved (executed). The actual order is partially determined during the sorting step in compilation. Once the compilation step has completed, the sorted order cannot be changed for the entire duration of the block diagram's execution.

Following the compilation stage, is the model link stage which may also produce linear models. After linking has been performed, code may or may not be generated. If code is generated, the model is simulated/executed through accelerated simulation mode in which the block diagram model (or portions of it) is translated into either software modules or hardware descriptions (broadly termed code). If this stage is performed, then the stages that follow use the generated code during the execution of the block diagram. If code is not generated, the block diagram may execute in interpretive mode in which the compiled and linked version of the block diagram may be directly utilized to execute the model over the desired time-span. This interpretive mode of execution is suitable for getting fine-grained signal traceability. There are several different advantages to execution through code generation. Execution of generated code can be more efficient than interpretive execution because of fewer data-structures and lesser internal messaging in the engine, although the increased efficiency generally comes at the cost of decreased execution traceability. Simulation of hardware descriptions during execution can help identify and resolve bugs in the software stage of a design project. Such bugs prove much more expensive to track and fix once the system has been implemented in hardware. Additionally, block diagram modeling software can be integrated with other software environments that are suitable for modeling and simulating special classes of systems. Models can be tested directly in hardware thereby making prototyping of new systems fast and cost-effective. Those skilled in the art will recognize that when users generate code, they may choose to not proceed further with the block diagram's execution. They may choose to take the code and deploy it outside of the confines of the modeling software environment. This is normally the last step in the design of dynamic systems in a block diagram software package.

In one particular embodiment the modeling environment 110 provides a tool allowing a user to select the complexity with which a model executes. Referring back to FIG. 4 as an example, a user can be provided with a choice of executing pathway 4100 as a simple input-output block or executing pathway 4100 in the more detailed form shown in FIG. 4.

Referring back to FIG. 1, the model created in the modeling environment 110 can be used by the simulation engine 120. Dynamic systems, such as biological processes and chemical reactions, are typically modeled as sets of differential, difference, algebraic, and/or recursive equations. At any given instant of time, these equations may be viewed as relationships between the system's output response ("outputs"), the system's input stimuli ("inputs") at that time, the current state of the system, the system parameters, and time. The state of the system may be thought of as a numerical representation of the dynamically changing configuration of the system. For instance, in a physical system modeling a simple pendulum, the state may be viewed as the current position and velocity of the pendulum. Similarly, a signal-processing system that filters a signal would maintain a set of previous inputs as the state. The system parameters are the numerical representation of the static (unchanging) configuration of the system and may be viewed as constant coefficients in the system's equations. For the pendulum example, a parameter is the length of pendulum and for the filter example; a parameter is the values of the filter taps. A simulation engine useful in connection with the present invention is Simulink, available from The MathWorks, Inc. of Natick, Mass.

Figure 5A:
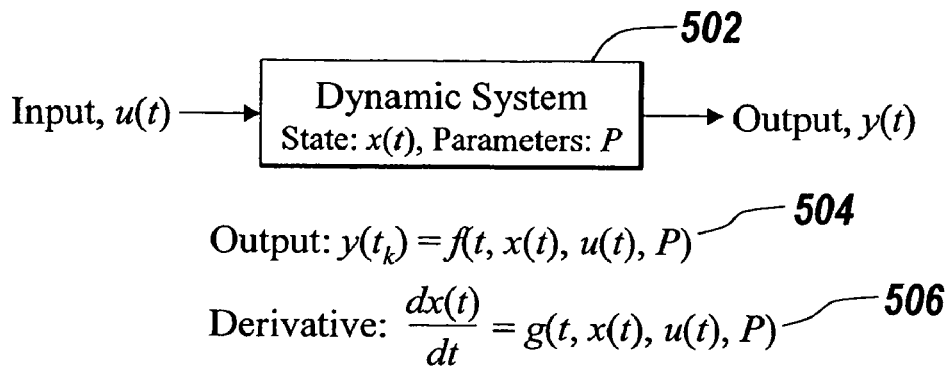
FIG. 5A is a block diagram depicting a model of a dynamic system using ordinary differential equations.

The present system adds a fifth type of mathematical model, stochastic models, to the types of mathematical models used in the study of dynamic systems: differential equations; difference equations; algebraic equations; and hybrid models. The first type of mathematical model describes systems using ordinary differential equations (ODEs) and is depicted in FIG. 5A. The dynamic system 502 specifies a set of two equations: Output 504 and Derivative 506. The Output equation 504 facilitates the computation of the system's output response at a given time instant as a function of its inputs, states, parameters, and time. The Derivative equation 506 is an ordinary differential equation that allows the computation of the derivative of the states at the current time as a function of the inputs, the states, parameters, and time. This class of models is suitable for systems in which it is important to track the system response as a continuous function of time. Such continuous-time systems are commonly representative of physical systems (mechanical, thermal, electrical) however, they may also be useful for chemical and biochemical reactions such as intracellular biochemical reactions. For example, continuous-time systems can be useful in modeling cellular metabolism while stochastic systems can be used to model cellular regulatory systems such as DNA transcription. For simple systems, it may be possible to use the Output 504 and Derivative equations 506 to obtain a closed-form solution for the output response y(t). But in most complex real world systems, the response of the system is obtained by integrating the states through numerical means.

The definition of an ODE used herein encompasses both implicit and explicit differential equations. The class of ordinary differential equations may require additional equations to define the system being modeled. For example, equations called projections may be required to impose constraints on the differential variables (e.g., states $X_1$ and $X_2$ must fall on the manifold defined by $x_1^2 + x_2^2 = 25$). These constraints can be applied as a coupled condition to the differential equation. Although systems including the projections may conventionally no longer qualify as an ODE; they are included here as differential algebraic equations to simplify the categories of systems. Another example is the use of a Jacobian equation that defines partial derivatives with respect to the independent and/or differential variables. The Jacobian equation is typically used when obtaining a linear approximation of a non-linear model or an overall linear model of a set of equations. Jacobian equations are required for some forms of numerical integration, for producing the linear model once the model has reached its steady state operating point, etc. The Output 504 and Derivatives equations 506 may be extended to define other relationships for the block. For example, the Output equation 504 may help manage its states by defining a relationship where it resets the state back to a known quantity at a specific point in time or when a specific condition is seen. Jacobians may also be used to perform Sensitivity Analysis of a modeled system. Sensitivity analysis identifies the variable critical to the system's behavior.

Figure 5B:
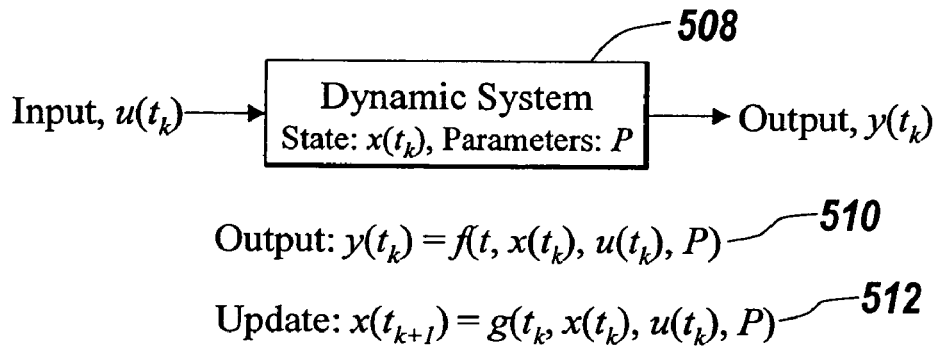
FIG. 5B is a block diagram depicting a model of a dynamic system using difference equations.
Figure 5C:
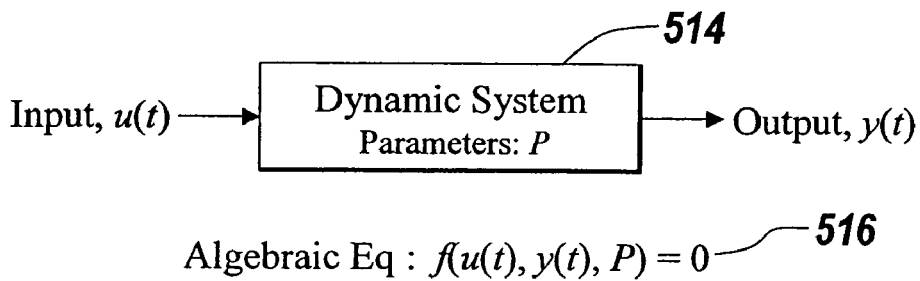
FIG. 5C is a block diagram depicting a model of a dynamic system using algebraic equations.
Figure 6:
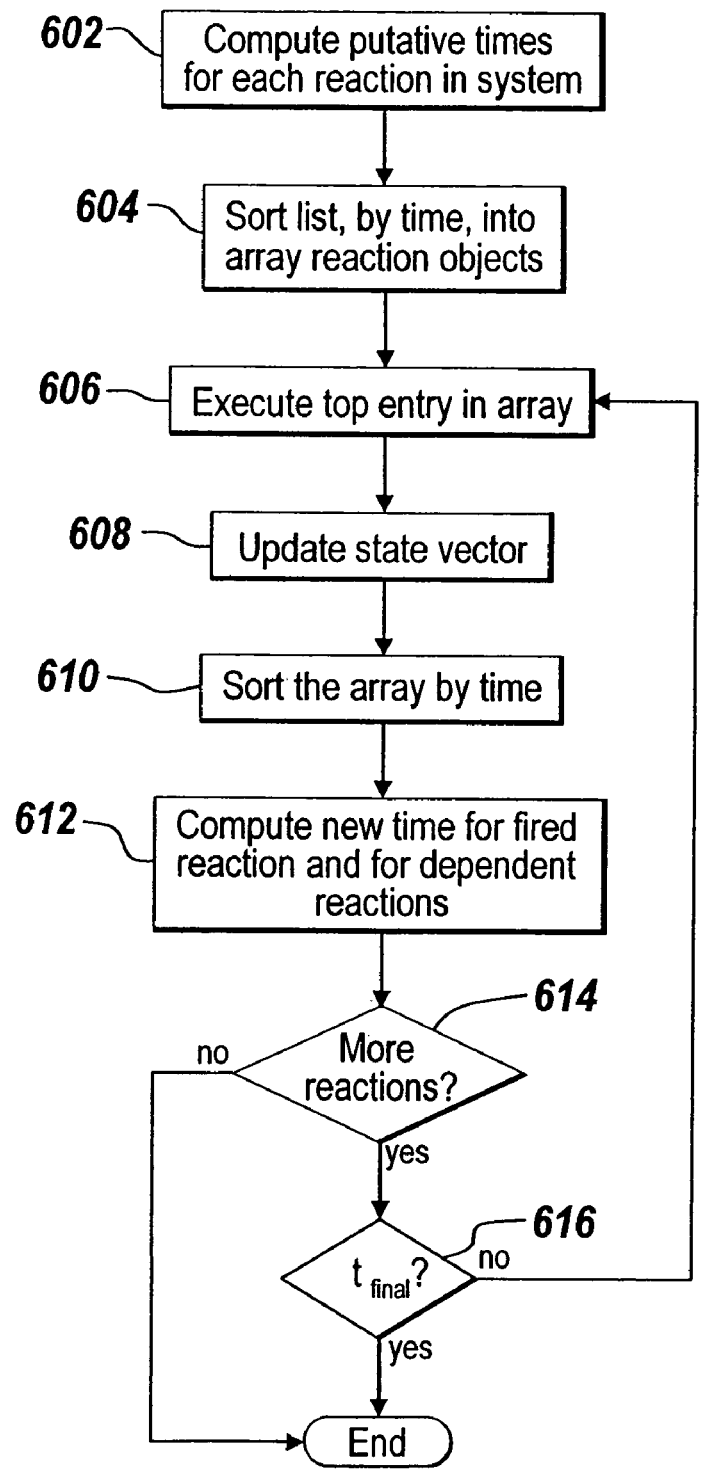
FIG. 6 is a flowchart depicting one embodiment of the steps taken to simulate a modeled biological process or chemical reaction.

Another type of mathematical model describes systems using difference equations as depicted in FIG. 5B. The dynamic system 508 specifies a set of two equations: Output 510 and Update 512. The Output equation 510 facilitates the computation of the system's output response at a given time instant as a function of the inputs, states at some previous time, parameters, and time. The Update equation 512 is a difference equation that allows the computation of the states at the current time as a function of the inputs, states at some previous time, parameters, and time. This class of models is suitable for systems in which it is important to track the system response at discrete points in time. Such discrete-time systems are typically representative of discrete-time control and digital signal processing systems. For simple systems, it may be possible to use the Output 510 and Update equations 512 to obtain a closed-form solution for the output response y(t). But in most complex real world systems, the response of the system is solved through recursion. The Output 510 and Update equations 512 are applied repeatedly to solve for the system response over a period of time. An additional type of mathematical model describes systems using algebraic equations as depicted in FIG. 5C. The dynamic system 514 uses an algebraic equation 516 that needs to be solved at each time to obtain the outputs. While simple systems may allow one to obtain a closed-form solution for the system inputs and outputs, practical algebraic equations may best be solved iteratively using a numerical method involving both perturbations and iterations. Algebraic equation solving techniques used in the context of dynamic system modeling are discussed in greater detail below.

For modeling biological processes and chemical reactions, an additional model is useful. This model describes systems using stochastic techniques, such as Gillespie, Gibson/Bruck, and T-leaping. These techniques are useful when the continuous approximation implied by ODE/DAE systems is not applicable. This may be the case when dealing with small molecule counts, such as RNA polymerase binding to DNA to transcribe a particular gene. An example of a chemical equation that could be treated stochastically is shown in the reactions table of FIG. 3B, e.g., s32+Dnak→s32:Dnak. This equation indicates that one molecule of s32 bonds with one molecule of Dnak. When simulated stochastically, this reaction occurs at a random time determined according to a probability distribution that depends on reaction kinetics. Various probability distributions may be used to determine when the reaction occurs, such as exponential distributions, binomial distributions, F distributions, frequency distributions, geometric distributions, hypergeometric distributions, multinomial distributions, negative binomial distributions, percentage distributions, percentage cumulative distributions, Poisson distributions, posterior distributions, prior distributions, t distributions and normal distributions. In other embodiments, the user may define a probability distribution to use when determining the time value for the occurrence of a stochastic reaction.

A fifth type of mathematical model is a composite system that has components that fall into the four types of models discussed above. Most complex real-world system models fall into this category. This class of systems has Output, Derivative, Update, and potentially other equations. Solving for the output response of such systems requires a combination of the solution approaches discussed for all of the classes above. One example of a composite system is one described by differential-algebraic equations (DAEs) which contain both differential equations and algebraic equations. Of particular interest in biochemical models is a hybrid approach that contains both stochastic and deterministic equations, which allows for the solving of both metabolic and regulatory systems in the same model.

Grouped within the composite class of systems are many extensions involving relationships (equations) defined in terms of both outputs and state. For example, one can define a limited integration relationship for a differential variable. This relationship requires a set of equations that consists of the Output equation, an Update equation, a Derivative equation, and a Zero Crossing equation. The Zero Crossing equation defines the points in time where the upper and lower limits of the limited integration occur. Another example of an extension is the notion of Enable and Disable equations that define relationships among states or signals when parts of a system are activated and deactivated during execution.

Inherent in four of the classes of systems (ODE, difference equations, algebraic equations and composite) is the notion of system sample time. The sample-time is the time interval at which the inputs, state, or outputs (collectively referred to as the results) of the system are traced as time progresses. Based on sample times, a system can be described as a discrete-time system, continuous-time system and hybrid system. As noted above, stochastic systems occur at a random time determined by an operative probability distribution.

A discrete-time system is a system in which the evolution of the system results is tracked at finite intervals of time. In the limit as the interval approaches zero, the discrete-time system becomes a continuous-time system. The intervals of time may be periodic or non-periodic. Sometimes, non-periodic rate systems, such as stochastic systems, are referred to as non-uniform rate systems meaning that there is no periodic rate at which the response can be tracked. A continuous-time system is a system in which the evolutions of the system results are continuously changing. Continuous-time signals change during numerical integration. An example of a continuous-time system is one described by an ODE. There can also be algebraic or composite continuous-time systems. A hybrid system is a system with both discrete-time and continuous-time elements.

If a system has only one sample time, it is said to be single-rate. If a system has multiple sample times, it is said to be multi-rate. Multi-rate systems can be evaluated (executed) using either a single-tasking form of execution or a multi-tasking form of execution. When multi-tasking execution is used, it conforms to rate monotonic scheduling principals as defined by Liu, C. L., and LAYLAND, J. W. *Scheduling Algorithms for Multiprogramming in a Hard-Real-Time Environment*. ACM 20, 1 (January 1973), 46-61. Systems may also be categorized by the type of numerical integration solver being used. A fixed-step system is one that uses a fixed-step solver. Fixed-step solvers typically use explicit methods to compute the next continuous state at fixed periodic intervals of time. A variable-step system is one that is using a variable-step solver. A variable-step solver can use either implicit or explicit methods to compute the next continuous state at non-periodic intervals of time. Generally, variable-step solvers use a form of error control to adjust the interval size such that the desired error tolerances are achieved.

In practice, except for the most basic systems, mathematical models for dynamic systems involve a complex set of mathematical transformations applied in some prescribed manner with the outputs of some transformations forming the inputs of others. Each elemental transformation may be viewed in isolation as a simple dynamic system falling into one of the categories listed above. Therefore, a complex dynamic system may be modeled as an interconnection of various simple dynamic systems. A schematic representation of such an interconnection that has evolved over the years is the block diagram. Such block diagram models have now become a standard means in textbooks, design papers, journal articles, and specifications to communicate the details of a dynamic system's behavior.

A block diagram model of a dynamic system is represented schematically as a collection of blocks interconnected by lines that represent the input and output of a dynamic system. Each block represents an elemental dynamic system. A line emanating at one block and terminating at another signifies that the second block is a product of the first block. Those skilled in the art will recognize that the term "blocks" does not refer exclusively to elemental dynamic systems but may also include other modeling elements that aid in readability and modularity of block diagrams.

The theory of Digital Signal Processing (DSP) focuses on modeling signals as sequences of samples. This view naturally fits into the time-based block diagram paradigm by mapping the samples u[n] to discrete-time points $u(t_k)$. This adds the benefit of being able to model the interaction between DSP systems and other classes of time-based systems, e.g. continuous and/or discrete-time control systems.

Put another way, block diagram models are time-based relationships between signals and state variables representative of a dynamic system. The solution (computation of system response) of the model is obtained by evaluating these relationships over time, where time starts at a user-specified "start time" and ends at a user-specified "stop time". Each evaluation of these relationships is referred to as a time step. Signals represent quantities that change over time, and these quantities are defined for all points in time between the block diagram's start and stop time. The relationships between signals and state variables are defined by sets of equations represented by blocks. These equations define a relationship between the input signals, output signals, state, and time. Inherent in the definition is the notion of parameters, which are the coefficients of the equations.

It is important to note that block diagrams are not exclusively used for representing time-based dynamic systems but also for other models of computation. For instance, flowcharts are block diagrams used to capture process flow and are not generally suitable for describing dynamic system behavior. Data flow block diagrams are block diagrams that describe a graphical programming paradigm where the availability of data (often thought of as tokens) is used to initiate the execution of blocks, where a block represents an operation and a line represents execution dependency describing the direction of data flowing between blocks. As used herein, the term block diagrams means time-based block diagrams used in the context of dynamic systems except as otherwise noted.

A block diagram execution engine contributes to the modeling software task of enabling the computation and tracing of a dynamic system's outputs manufactured by its block diagram model. An execution engine carries out the task of compiling and linking the block diagram to produce an "in-memory executable" version of the model that is used for generating code and/or simulating or linearizing a block diagram model. Execution of the block-diagram is also referred to as simulation. The compile stage involves checking the integrity and validity of the block interconnections in the block diagram. In this stage, the engine also sorts the blocks in the block diagram into hierarchical lists that are used when creating the block method execution lists. In the link stage, the execution engine uses the result of the compiled stage to allocate memory needed for the execution of the various components of the block diagram. The linking stage also produces block method execution lists which are used by the simulation or linearization of the block diagram. Included within the link stage is the initialization of the model which consists of evaluating "setup" methods (e.g. block start, initialize, enable, and constant output methods). The block method execution lists are generated because the simulation and/or linearization of a model must execute block methods by type (not by block) when they have a sample hit.

After linking has been performed, the execution engine may generate code. In this stage, the execution engine may choose to translate the block diagram model (or portions of it) into either software modules or hardware descriptions (broadly termed code). If this stage is performed, then the stages that follow use the generated code during the execution of the block diagram. If this stage is skipped completely, then the execution engine uses an interpretive mode of execution for the block diagram. In some cases, the user may not proceed further with the execution of the block diagram because they would like to deploy the code outside the confines of the block diagram software. Upon reaching the simulation stage, the execution engine uses a simulation loop to execute block methods in a pre-defined ordering upon a sample hit to produce the system responses they change with time.

Determination of putative reaction times relies on the size of time intervals chosen for the simulation. In order to understand how the step size is picked, it is first necessary to understand the notion of a solver. The solver is a module of the simulation engine 120 that is responsible for performing two tasks: (a) determining how far execution time should be advanced between consecutive passes in order to accurately trace the system's outputs, and (b) integrating the derivative of the states of the system to obtain the actual states. Based on how solvers perform the first task, they are generally classified into two basic classes: fixed-step solvers or variable-step solvers.

Fixed-step solvers are solvers in which the time step-size between consecutive passes is a fixed quantity. The user generally explicitly specifies this quantity. These solvers are used to model types of systems that must operate within a defined time (discrete systems). For instance, an anti-lock braking system may be designed to control a car's braking system, and to execute such control in one-one hundredth (0.01) of a second so as to assure the car stops safely; if the braking system does not meet its timing constraints, the car may crash. Fixed-step solvers, therefore, are designed to help model discrete systems that have to generate a result in a fixed time period, and the fixed-step execution assures that the modeled system can generate such results. Some reactions may be defined as having a discrete sample time, in which case the value of the reaction could be calculated at fixed intervals using a fixed-step solver.

However, some reactions are defined to be a continuous-time system. For these reactions, event scheduling occurs at time intervals that are determined by the simulation engine to minimize accumulation of errors. These reactions require use of variable-step solvers, which are designed to model continuous systems where non-evenly spaced time steps are needed to simulate all significant behavior. For example, one may want to simulate the path of a bouncing ball, where it bounces, how high it bounces, and where it stops. It is known, based on experience, that the ball's bounces will not be evenly spaced, and that the height of the bounces will diminish as a result of gravity, friction, and other forces. Variable-step solvers are used for these types of continuous systems and to determine what step size to use so that the behavior of the ball will be accurately modeled.

In still other embodiments, reactions that are considered "fast" by the model are assumed to have completed at "zero time," which effectively means that they are treated throughout model simulation as a constant having the value of the final result.

As noted previously, stochastic reactions occur at a random time based on an operative probability distribution, which do not neatly fit either type of solver. In order to adequately model systems including stochastic reactions, either alone or as part of a hybrid system including both stochastic and either fixed-solver elements or variable-solver elements, the following steps may be taken.

The simulation determines putative times for each reaction in the model (step 602). Once putative reactions times are computed for each reaction in the system, the times are sorted, by putative occurrence time, into a state array (step 604). In one embodiment, the state array is an array of pointers sorted by occurrence time, each of the pointers pointing to the object to be executed at that point in model simulation. Once sorted, the object identified by the first entry in the array is executed (step 606).

Because execution of the top object may affect the amount of species present in the modeled system or the putative reaction times for specific reactions in the table, the putative time for each of the entries in the state array is recalculated (step 608) and the state array is resorted (step 610).

The simulation engine 120 checks for additional reactions to execute (step 614). If additional reactions exist, the simulation engine 120 checks to determine in the final simulation time has been reached (step 616). If not, the simulation engine 120 executes the next entry in the state array (step 606). Otherwise, the simulation terminates. One of ordinary skill the art would recognize that other scheduling methodologies may be used.

In one embodiment the simulation engine 120 provides a mechanism for storing the entire simulation context, and a mechanism for restoring the entire simulation context. In one aspect of the present invention, before simulation is started, a flag is set in the modeling environment 110 instructing the simulation environment 120 to store simulation context when the simulation finishes (either because the final time is reached, simulation was interrupted by the user, or otherwise). Alternative procedures for querying whether the context should be stored or not may also be implemented (e.g., user interaction when a simulation is finished). Once the simulation finishes, the simulation context may be stored as a file, in a workspace parameter, or in some other format.

In one embodiment, the simulation context is stored to file. The file into which the simulation context is stored may be automatically named. However, a user-defined file may be used alternatively. The storage mechanism for saving the simulation context can vary from saving the context as memory dump, to saving the context memory as a platform independent textual dump through a conversion process. As long as there are no architectural incompatibilities between computer architectures involved there will be no differences in the results. Other implementations such as saving the context as a platform independent binary dump or a platform dependent textual dump are also within the scope of the present invention.

The user interface of the context restoration is achieved by starting the simulation with a corresponding 'continue simulation' command. This may be implemented as a parameter for the normal means to trigger simulation or any other way. A continued simulation takes as arguments all arguments (mandatory and optional) of an initial simulation such as final time and additional output times.

To store simulation context, a 'StoreSimulationContext' flag may be set in the simulation engine 120 or it may be communicated to the simulation engine 120 by the analysis environment 130. Other implementations, such as using graphical elements in the modeling environment 110, may be used instead or in addition to the use of a flag. Additionally, context storage can be an activity that occurs during simulation (i.e., without interrupting a regulation simulation). To this end, the user may specify particular storage conditions (e.g., when a certain point in time is reached in simulation such as the achievement of a steady state or when particular values of model variables exist). This could result in a sequence of simulation context files with snapshots of the simulation context over the course of a simulation run.

In one embodiment, the simulation engine 120 registers areas of memory that constitute the simulation context, and subsequently calls a procedure to store and restore the simulation context. In one embodiment, the simulation context related areas in memory are registered before a simulation is started. This is implemented by rerouting the general memory allocation call through a registration mechanism. A complication in storing and restoring the simulation context arises when aggregate variables mix references and values. To illustrate this, consider the attributes of a Runge-Kutta 45 solver. In its C++ implementation, the class RK45 is derived from VarStepSolver. The attributes of RK45 are

```
RK45
    double t0;
    double *x0;
    double t1;
    double *x1;
    double h;
    double *dX[7];
    bool projectInterpolant;
    static const int id;
    static const double power;
```

Figure 7:
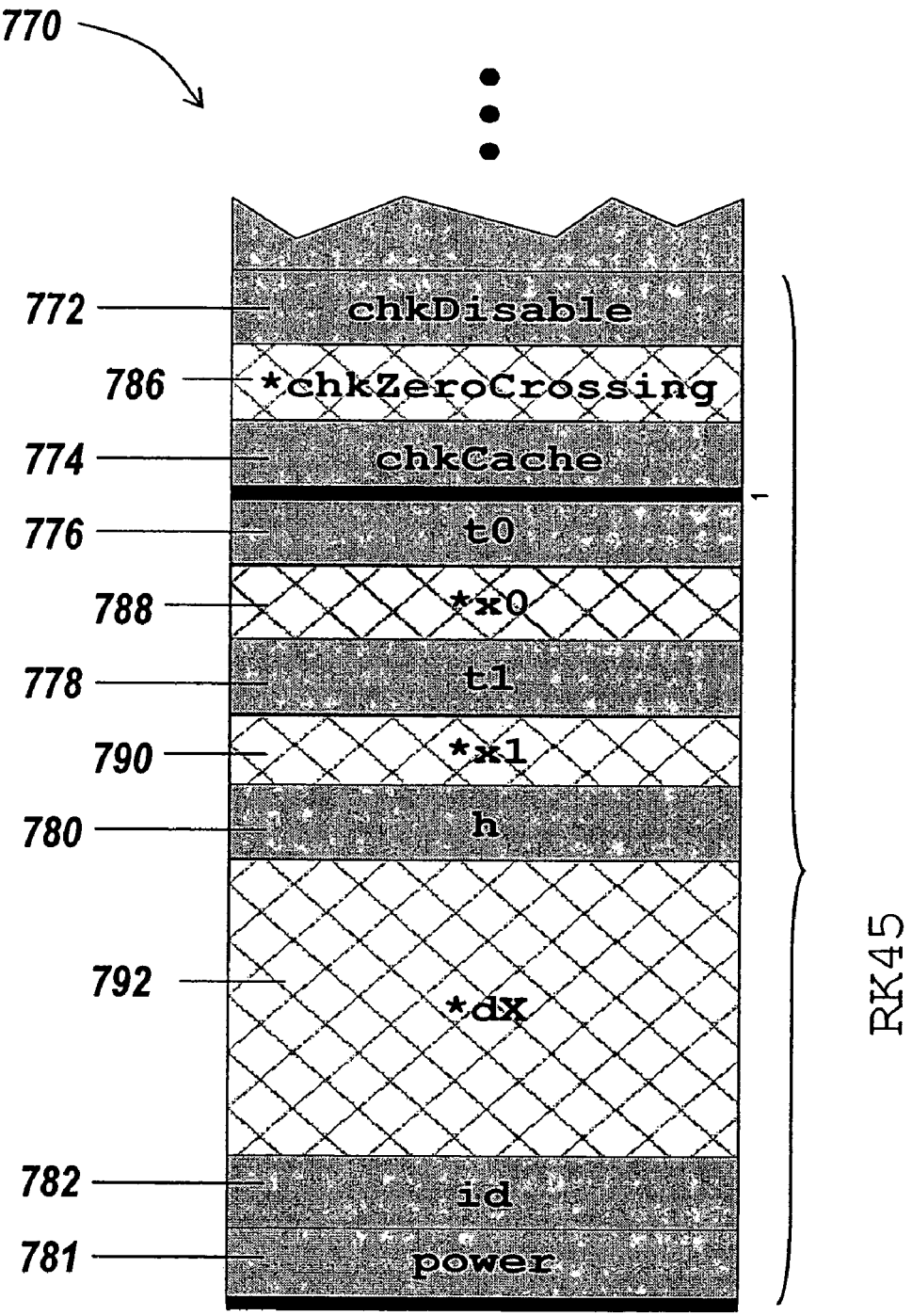
FIG. 7 depicts a block diagram of the allocated memory for a solver.

The definition reveals that an instance of RK45 contains value attributes and reference attributes. The references contain pointers specific to the particular simulation and they may differ between simulation runs. So, restoring these may result in invalid references, and, therefore, these should be excluded. FIG. 7 depicts part of the allocated memory 770 for an instance of RK45. The allocated memory includes value fields 772, 774, 776, 778, 780, 782 and 784 and reference fields 786, 788, 790 and 792.

Two basic approaches exist for tracking the simulation context memory allocations. A localized indexing scheme tracks the pertinent variables of an object that is part of the context. Alternatively, a global table may be maintained. The first approach lends itself well to the object-oriented coding paradigm whereas the second approach is more suitable to a procedural style of coding. Those skilled in the art will recognize that other methods of identifying and noting the portions of memory used by the simulation context may be employed within the scope of the present invention.

In the case of a global indexing scheme, the pertinent variables are identified by a special call when they are defined, i.e., when their memory is allocated. To this end, instead of calling standard run-time allocation procedure, an intermediate function call is used that calls the allocation procedure as done otherwise, but before it returns, it registers the allocated memory as being part of the context.

Note that the indexing scheme can be extended to store local model information to facilitate selective context restoration. As such, the context of a subsystem in a model can be identified and restored upon request, even in case of model changes elsewhere that affect the memory layout of those parts. The preferred embodiment tracks the instances of model parts and the memory they allocate, which is then assigned a unique identifier.

With the modularization of the numerical solvers, and the initiative to increasingly apply object-oriented coding principles, the need for a more distributed implementation has emerged. In this architecture, it becomes desirable not to have a global index of pertinent memory, but to maintain this locally for each object. A context sensitive object implements an access method to make its context available. Several implementations are possible. For example, an object could produce an index to each memory location that is part of the context and have the streaming operation performed by the caller, or it could stream the memory content itself.

This local indexing scheme supports selective memory restoration for parts of the model (e.g., one subsystem only) as it is object based Indexing the origin in the model of context fragments, optionally combined with a conversion mechanism between type implementations, allows restoration between platforms and different compiled versions of models. This supports, e.g., having a controller reach a steady state operating point in simulation in combination with a detailed phenomenological plant model, storing the context, and then after generating code for the controller, using the same context to initialize the controller code.

The type of the indexing being used, centralized or distributed has to be selected. This is related to the coupling of the indexing to the memory allocation calls: A table keeps track of the parts of memory that are part of the context. When memory for an instance is allocated, it is indexed as being part of the context which allows restoring it. A straightforward approach indexes all the RK45 specific memory of this instance by <address, size> tuples. Given the base address of the RK45 instance and the size of its type, the entire part of memory is considered part of the context.

Figures 8A, 8B:
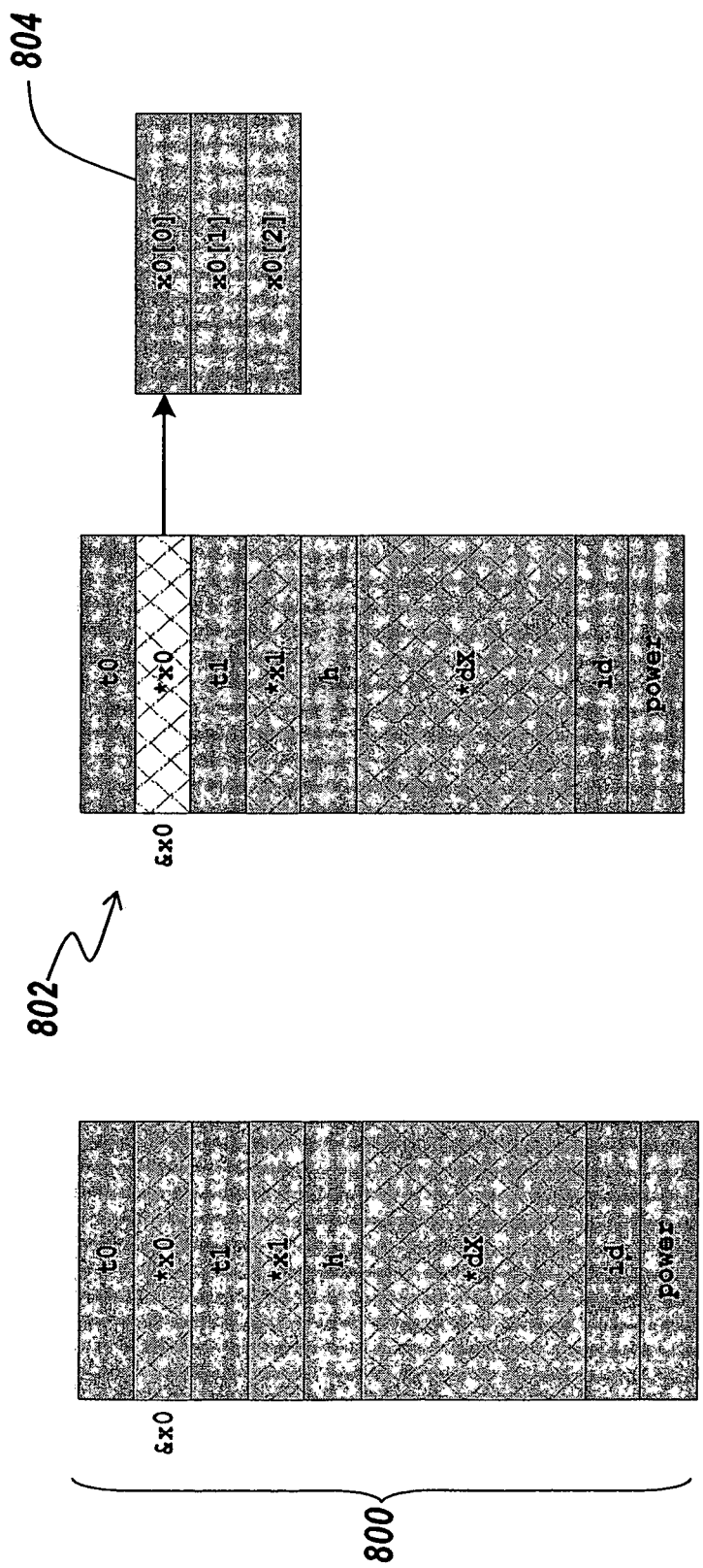
FIG. 8A depicts a block diagram of the allocated memory for a solver showing the part of memory holding both values and references.
FIG. 8B depicts a block diagram of the allocated memory for a solver showing the part of memory holding both values and references and the parallel indexing of only references.

In order to exempt the referencing part of memory, the memory allocation call for the referenced variables can be exploited. This prevents redundancy that would be required when the type definition would explicitly exclude referenced parts of memory. This approach is illustrated in FIG. 8A. When the RK45 instance is defined, an <address, size> tuple marks the corresponding part of memory 800, including both values and references. Next, when one of the referenced variables, x0, is defined, in FIG. 8B, an <address, size> tuple is created that marks the memory 802 where its values are located. In the same function, a <address, size> tuple is created as part of a parallel indexing scheme 804 that keeps track of areas in memory with references. Thus one implementation of the present invention includes two indexing schemes with <address, size> tuples, one for the context related memory with both values and references 800 and one for the parts of this memory 802 that contain references. This implementation allows the exploitation of allocation calls for indexing. Alternatively, the <address, size> tuple in the memory indexing scheme with references could be partitioned when one of these referenced variables is defined. This requires a somewhat more sophisticated registration mechanism. In an alternate implementation, the memory area is not dynamically constructed but hard-coded as the set of variables that are part of the context. Both indexing schemes are implemented and used in conjunction with one another.

Since the work arrays of user defined functions are part of the indexed memory, no additional effort is required to make a user defined block adhere to the restoration scheme as long as variables are declared through the standard interface. For example, the interface to declare continuous state variables is ssSetNumContStates(S, NUM_CONT_STATES), where S references the user-defined system and NUM_CONT_STATES the number of continuous states. To facilitate more flexibility, an option for the user to stream selected variables to and from file is also implemented for user defined blocks.

Due to the indexing scheme for the areas in memory that need to be stored and restored, a mechanism is required to invoke the indexing operations and to facilitate the context restoration. It is important to note that the memory that is part of the context is all allocated when a simulation run is requested. It has to be indexed anew before each simulation is executed because changes to the execution may have been made (e.g., a different solver may have been chosen).

The restoration process is implemented around the main simulation loop as shown in italics in the following code snippet:

```
int SimulateModel(slModel *model, CmdlInfo *cmdlInfo)
{
    ...
    sm_SimStatus(model, SIMSTATUS_RUNNING);
    if( slLoadContext(model)) ssSetTFinal(S, getCtxTFinal( ));
    while (ssGetT(S) < ssGetTFinal(S)) {
        ...
    }
    slCtxStore(model); /*store context for possible continuation*/
    if (!stopRequested) {
        ssSetStopRequested(S,true);
        errmsg = slDoOutputAndUpdate(model);
        if (errmsg != SL\_NoError) return(errmsg);
    }
    ...
    return(errmsg);
} /* end SimulateModel */
```

Before a simulation starts, it is determined whether the simulation context needs to be restored by means of a call to slLoadContext which is executed in the same function call in cases where the restore flag is set. Once the context is restored, simulation proceeds as if invoked normally. Once completed, the indexed memory is stored by the slCtxStore call if the StoreSimulationContext flag of the block diagram is set by the user. The context is written to a file with an mcx extension in one implementation.

Figure 9:
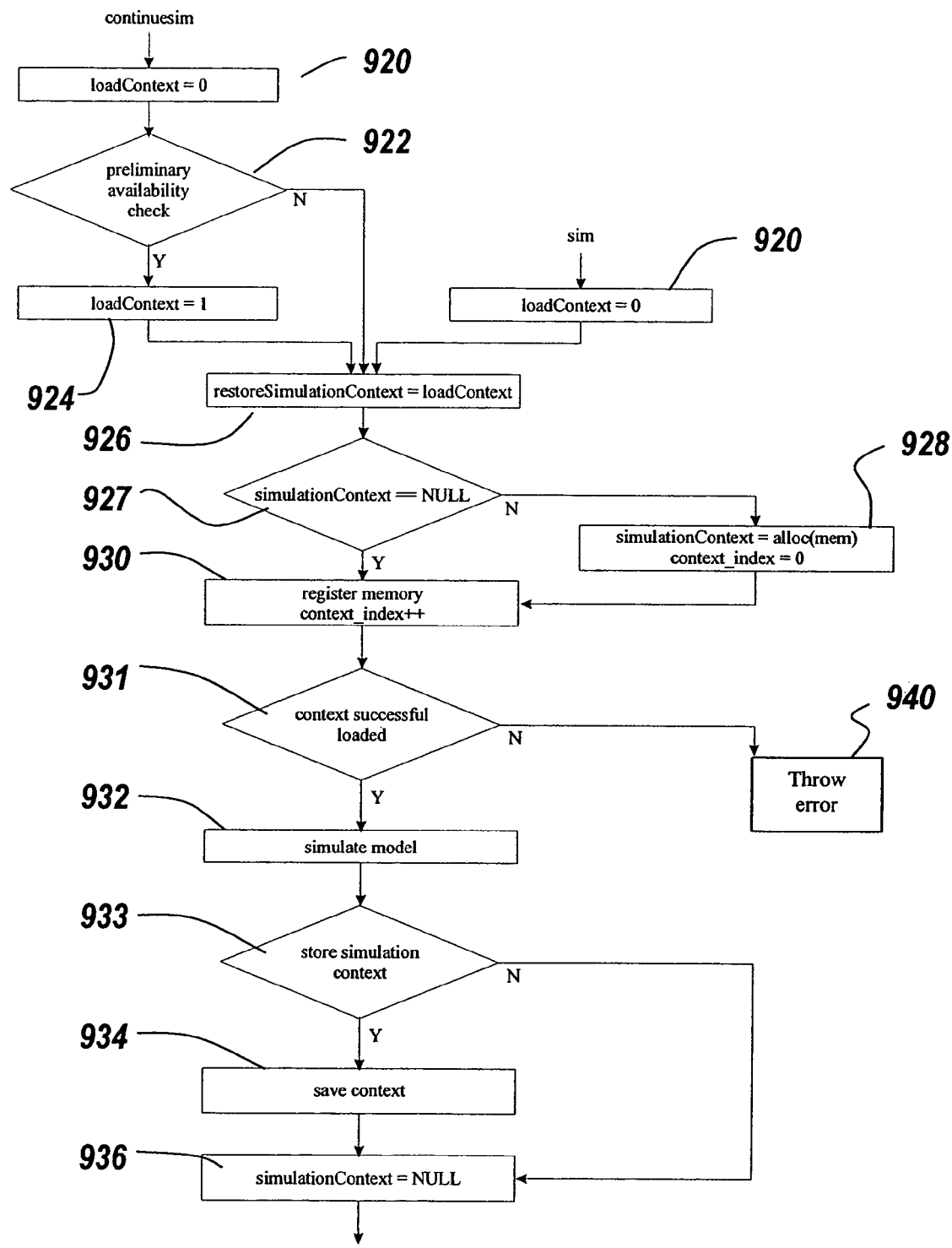
FIG. 9 is a flow chart of the sequence of steps followed by the illustrative embodiment of the present invention to implement the restoration mechanism prior to execution.

The flow chart in FIG. 9 depicts the implementation of the restoration mechanism. The context indexing is initiated when a model attribute simulationContext is not yet set. This is to ensure that when a new simulation run is requested, the originally indexed memory is cleared and reassigned. Otherwise, it would be appended and the same area in memory would be indexed an increasing number of times (related to the number of times a simulation was run). As soon as the context is written to file by slCtxStore, or in case of another exit path (e.g., because of error conditions) simulationContext is reset to indicate that a new simulation run may start.

When a new run is initiated, the first context redirected allocation call resets ContextInitializationComplete, resets the index, and creates the first <address, size> tuple. Consecutive allocation calls then complete the memory index, including the scheme that indexes the parts of context memory that contain references instead of values. This functionality is required at all times (i.e., also when the context is not restored) since it facilitates context storage. A determination is then made as to whether the user requested a simulation continuation, indicated by the loadContext flag. If so, the model checksum that captures the memory map of the model of the stored context is validated and when it complies with the checksum of the model to be simulated, the context is restored. This is important because the model memory map has to be compatible with that of the model used to save the simulation context. The main simulation loop is then executed and when completed the present simulation context is written to file. It should be noted that the context save has to be done before the slDoOutputAndUpdate that follows because in case of a fixed step size, evaluating slDoOutputAndUpdate puts the state of the discrete pulse generator to the next point time, but restart continues from the current point.

FIG. 9 depicts the sequence of steps by which the simulation engine may restore simulation contexts and then execute. The sequence begins with the loadContext variable set to zero (step 920). A determination is made as to whether a stored simulation context is available (step 922). If one is available, the loadContext variable is set to one (step 924). Next, the restoreSimulationContext variable is set to equal the loadContext variable (step 926). If the simulationContext variable is not set (step 927), memory is assigned (step 928). Next, the simulationContext memory is loaded (step 930) and confirmation of the loading is made (step 931). If the simulation context has been restored, simulation takes place (step 933). The simulation context may be saved following simulation depending upon the user's wishes (step 933) determined either prior to simulation or interactively. If the simulation context is to be saved, it is saved (step 934) and the simulationContext variable reset to NULL (step 936) while freeing the assigned memory. If the simulation context is not being saved, the simulationContext value is still set to NULL (step 936).

The restored simulation context may be used to run multiple analyses from a common reproducible point to test alternatives. The restored simulation context may be used to run the alternative analyses simultaneously in parallel. In other embodiment, the simulation context may be used to update a construction model. The restoration of the simulation context saves significant time over previous simulation methods by ensuring accuracy despite not having to re-run a simulation for transitory or initialization stages of a simulation. Multiple simulation contexts may also be saved from a running simulation without stopping the simulation thus helping in debugging and other types of analysis. The illustrative embodiment of the present invention enables simulation of a wide variety of systems and is not limited to time-based block diagrams.

In another embodiment, the simulation of reversible reactions is optimized. In these embodiments, the state array is parsed to identify whether "both directions" of a reversible reaction occur at the same simulation time in the state array, i.e., the next two reactions to be simulated are C→Br and Br→Ce. When this occurs, both reactions are skipped, since they cancel one another out. Using well-known code optimization techniques, this concept may be extended to three or more reactions that, together, cancel one another out, e.g., Ce→Br, Br→Pb, Pb→Ce.

Referring again to FIG. 1, the results generated by the simulation engine 120 may be used by an analysis environment 130. In other embodiments, the analysis environment 130 operates directly on a model to, for example, generate a steady-state value for a modeled system instead of simulating the system. In some of these embodiments, the analysis tool 120 does this by setting the derivative of all differential equations to 0 and solving the system algebraically. In others of these embodiments, the analysis engine performs a flux-balance analysis, as is known in the art, to determine the steady-state value of a system. Other well-known forms of analysis that may be employed by the analysis environment 120 include using non-linear solvers, sensitivity analysis, bifurcation analysis, parameter scans, parameter estimation and network inference analysis. The result of these analyses may be provided to the simulation engine 120 as input for its calculations.

The analysis environment 130 may further process the results generated by the simulation engine 120 or it may display the results visually or auditorially. For example, the analysis environment 120 may use graph visualization techniques to identify to a user similar pathways. In some embodiments the analysis environment 130 interfaces with data acquisition hardware (not shown in FIG. 1) which allows the analysis environment 130 to compare the generated results with experimental data. In these embodiments, data gathered from an ongoing experiment is used to correct or generate a model of the reaction that is occurring in situ. In some embodiments the experiment is conducted on a microarray or a gene chip. For example, if the existence of a given protein is predicted by a model but data acquired from the experiment indicates that the protein does not exist, the analysis tool 130 may signal a user, either auditorially or visually, that the in situ experiment and the predicted response differ. For embodiments in which the experiment is conducted on a microarray, the gathered data may differ between microwells. In these embodiments, the analysis tool may average the value of the gathered data. In others of these embodiments, the analysis environment 130 may signal a difference if the data from a single microwell differs from the model's predicted response. In some embodiments, the amount of tolerable difference between the in situ experiment and the predicted result is user-configurable. In other embodiments, the analysis tool transmits the gathered data to the modeling environment 110 so that the model may be modified to account for the difference. In still other embodiments, the analysis environment 130 graphically displays the expected result of the experiment and data gathered from the experiment.

In other embodiments, the data acquisition hardware allows the analysis tool to control an experiment that is in progress based on the results generated by the simulation engine 120. These embodiments may be useful in construction of nanomachinery. In these embodiments, a model may call for in situ temperature to be at 102 degrees Fahrenheit. If a thermocouple measuring temperature of the in situ environment indicates that the temperature has fallen below 102 degrees Fahrenheit, more heat may be applied to the experiment.

Data acquisition hardware may include any of a number of hardware devices compatible with the computing platform executing the integrated modeling, simulation, and analysis environment 100. For example, in embodiments in which the environment 100 executes on a personal computer, the data acquisition hardware interfaces with the local system bus 220. In embodiments such as those shown in FIG. 2B, the data acquisition hardware interfaces with the HyperTransport bus, Rapid I/O bus, or InfiniBand. The data acquisition hardware can communicate with instruments and experiments that use GPIB (IEEE-488, HPIB), VISA, TCP/IP, and UDP standards.

Although the systems and methods of the present invention have been described above as executing on a single machine, they may also be used in a client-server environment such as X-Windows or Microsoft Terminal Services. The modeling environment 110, simulation engine 120, and analysis environment 130 may each execute on separate machines, or they may be aggregated in any combination between machines. For example, in one particular embodiment, the modeling environment 110 and the analysis environments 130 execute on a "client" machine while the simulation engine executes on a "server" machine. In these embodiments, the computers may be connected via a number of network topologies including bus, star, or ring topologies. The network can be a local area network (LAN), a metropolitan area network (MAN), or a wide area network (WAN) such as the Internet. And the respective computers may connect to the network 180 through a variety of connections including standard telephone lines, LAN or WAN links (e.g., T1, T3, 56 kb, X.25), broadband connections (ISDN, Frame Relay, ATM), and wireless connections. Connections can be established using a variety of communication protocols (e.g., TCP/IP, IPX, SPX, NetBIOS, NetBEUI, SMB, Ethernet, ARCNET, Fiber Distributed Data Interface (FDDI), RS232, IEEE 802.11, IEEE 802.11a, IEE 802.11b, IEEE 802.11g and direct asynchronous connections).

An embodiment of the present invention relates to a computer storage product including a computer-readable medium having computer code thereon for performing various computer-implemented operations. The media and computer code may be those specially designed and constructed for the purposes of the present invention, or they maybe of the kind well known and available to those having skill in the computer software arts. Examples of computer-readable media include, but are not limited to: magnetic media such as hard disks, floppy disks, and magnetic tape; optical media such as CD-ROMs, CD-R/RW discs, DVD-ROMs, DVD-RAMs, and holographic devices; magneto-optical media such as floptical disks; solid-state memories such as flash drives, memory sticks, xD cards, MultiMedia cards, and Smart Media cards; and hardware devices that are specially configured to store and execute program code, such as application-specific integrated circuits ("ASICs"), field-programmable gate arrays (FPGAs), programmable logic devices ("PLDs"), read only memories ("ROMs"), random access memories ("RAMs"), erasable programmable read only memories ("EPROMs"), and electrically erasable programmable read only memories ("EEPROMs").

Examples of computer code that may be embodied on such computer-readable media include machine code, such as produced by a compiler, and files containing higher level code that are executed by a computer using an interpreter. For example, an embodiment of the invention may be implemented using Java, C++, or other object-oriented programming language and development tools.

While the present invention has been described with references to various specific embodiments, it should be understood by those skilled in the art that various changes may be made and equivalents substituted without departing manufactured by the spirit and scope of the invention defined by the appended claims. In addition, modifications may be made to adapt to a particular situation, material, composition of matter, method, process, series of steps to the objective of the present invention while staying within the spirit and scope of the invention and such modifications are intended to be within the scope of the appended claims. In particular, while the methods disclosed have been described with reference to particular steps in a particular order, it will be understood that these steps may be combined, sub-divided, or reordered to form an equivalent method without departing manufactured by the teachings of the present invention. Accordingly, unless specifically indicated herein, the order and grouping of steps is not a limitation of the present invention.

What is claimed as new and desired to be protected by Letters Patent of the United States is:

1. A system for improved simulation of a biological system comprising a plurality of chemical reactions, the system comprising:
   a storage; and
   a processor for:
      constructing a graphical model of a biological system, the graphical model of the biological system comprising at least one chemical reaction, the at least one chemical reaction represented using a wild card character that allows multiple instances of an expression to be identified using a single reaction, and a merge block having an input and an output, the output of the merge block at a time step during an execution of the graphical model being equal to a most recent input provided to the merge block,
      accepting as input the constructed graphical model of the biological system, and
      executing the graphical model to generate as output dynamic behavior of the biological system by using the merge block and the at least one chemical reaction to produce a set of reactions described by the multiple instances of the expression.

2. The system of claim 1 wherein the graphical model is a block diagram model of the biological system.

3. The system of claim 2 wherein the processor is further configured to provide at least one block identifying a set of related chemical reactions.

4. The system of claim 1 wherein the processor is further configured to provide a graphical user interface for accepting user commands and data.

5. The system of claim 1, wherein the processor is further configured to display the dynamic behavior of the biological system.

6. A method for simulation of a biological system, the method comprising:
   constructing, using a computing device, a graphical model of the biological system, the graphical model of the biological system comprising at least one chemical reaction, the at least one chemical reaction represented using a wild card character that allows multiple instances of an expression to be identified using a single reaction, and a merge block having an input and an output, the output of the merge block at a time step during an execution of the graphical model being equal to a most recent input provided to the merge block;
   executing, using the computing device, the graphical model to generate dynamic behavior of the modeled biological system by using the merge block and the at least one chemical reaction to produce a set of reactions described by the multiple instances of the expression.

7. The method of claim 6 wherein constructing further comprises:
   constructing a block diagram model of the biological system.

8. The method of claim 7 wherein the block diagram model includes at least one block identifying a set of related chemical reactions.

9. The method of claim 6 wherein constructing further comprises:
   accepting user commands and data; and
   constructing the graphical model of the biological system using the user commands and data.

10. An article of manufacture having embodied thereon computer-readable instructions for improved simulation of a biological system comprising a plurality of chemical reactions, the article of manufacture comprising:
    computer-readable instructions for constructing, using received user commands and data, a graphical model of a biological system, the graphical model of the biological system comprising at least one chemical reaction, the at least one chemical reaction represented using a wild card character that allows multiple instances of an expression to be identified using a single reaction, and a merge block having an input and an output, the output of the merge block at a time step during an execution of the graphical model being equal to a most recent input provided to the merge block;
    computer-readable instructions for executing the constructed composite graphical model of the biological system to generate dynamic behavior of the modeled biological system by using the merge block and the at least one chemical reaction to produce a set of reactions described by the multiple instances of the expression.

11. The article of manufacture of claim 10 further comprising computer-readable instructions for displaying the dynamic behavior that is generated.

12. The article of manufacture of claim 10 wherein the computer-readable instructions for constructing a graphical model of the biological system comprises computer-readable instructions for constructing a block diagram model of the biological system.

13. The article of manufacture of claim 10 wherein the computer-readable instructions for constructing a block diagram model of the biological system includes computer-readable instructions for constructing at least one block identifying a set of related chemical reactions.

14. A system for simulation of a biological system, the system comprising:
    means for constructing a graphical model of the biological system, the graphical model of the biological system comprising at least one chemical reaction, the at least one chemical reaction represented using a wild card character that allows multiple instances of an expression to be identified using a simple reaction, and a merge block having an input and an output, the output of the merge block at a time step during an execution of the graphical model being equal to a most recent input provided to the merge block;
    means for executing the graphical model to generate dynamic behavior of the modeled biological system by using the merge block and the at least one chemical reaction to produce a set of reactions described by the multiple instances of the expression.

15. A computer-readable storage medium holding computer-executable instructions for simulation of a biological system, the medium comprising one or more instructions for:

constructing a graphical model of the biological system, the graphical model of the biological system comprising at least one chemical reaction, the at least one chemical reaction represented using a wild card character that allows multiple instances of an expression to be identified using a single reaction, and a merge block having an input and an output, the output of the merge block at a time step during an execution of the graphical model being equal to a most recent input provided to the merge block, the multiple instances of the expression representing at least a first chemical reaction and a second chemical reaction;

calculating putative reaction times for execution of the first chemical reaction and the second chemical reaction in the graphical model;

sorting the putative reaction times;

executing one of the first chemical reaction and the second chemical reaction identified by a first reaction, the first chemical reaction and the second chemical reaction being executed using the merge block and the at least one chemical reaction represented using a wild card character;

recalculating the putative reaction times for the first chemical reaction and the second chemical reaction after the executing of the first chemical reaction or the second chemical reaction; and sorting the recalculated putative reaction times.

16. The medium of claim 15, further comprising:
instructions for iterating execution of the instructions for executing, the instructions for recalculating and the instructions for sorting the recalculated putative reaction times until a final simulation time has been reached to generate a dynamic behavior of the modeled biological system.

17. The method of claim 6, further comprising:
annotating the composite graphical model in response to a user requesting to add annotations to the model that are provided by the user.

18. The system of claim 1, wherein the processor further stores the dynamic behavior of the biological system in the storage.

19. The method of claim 6, further comprising storing the dynamic behavior of the modeled biological system in a storage device.

20. The article of manufacture of claim 10, further comprising computer-readable instructions for storing the dynamic behavior of the modeled biological system in a storage.

* * * * *

UNITED STATES PATENT AND TRADEMARK OFFICE
CERTIFICATE OF CORRECTION

PATENT NO. : 8,296,070 B2
APPLICATION NO. : 10/783624
DATED : October 23, 2012
INVENTOR(S) : Ricardo E. Paxson et al.

It is certified that error appears in the above-identified patent and that said Letters Patent is hereby corrected as shown below:

In the Specification

Column 28, line 38, change "maybe" to "may be"

Signed and Sealed this
Twenty-third Day of July, 2013

Teresa Stanek Rea
*Acting Director of the United States Patent and Trademark Office*